US008222434B1

(12) United States Patent
Greenberg et al.

(10) Patent No.: US 8,222,434 B1
(45) Date of Patent: Jul. 17, 2012

(54) BACTOBOLIN ANALOG AND SYNTHESIS METHOD THEREOF

(75) Inventors: E. Peter Greenberg, Seattle, WA (US); Josephine R. Chandler, Seattle, WA (US); Breck Duerkop, Dallas, TX (US); Patricia Silva Lima, Duque de Caxias (BR); Joshua Alan Blodgett, Boston, MA (US); Jon Clardy, Boston, MA (US); Mohammad R. Seyedsayamdost, Newton, MA (US)

(73) Assignees: University of Washington through its Center for Commercialization, Seattle, WA (US); President and Fellows of Harvard College, Cambridge, MA (US)

( * ) Notice: Subject to any disclaimer, the term of this patent is extended or adjusted under 35 U.S.C. 154(b) by 67 days.

(21) Appl. No.: 12/754,599

(22) Filed: Apr. 5, 2010

Related U.S. Application Data

(60) Provisional application No. 61/166,729, filed on Apr. 4, 2009, provisional application No. 61/168,589, filed on Apr. 11, 2009, provisional application No. 61/260,806, filed on Nov. 12, 2009.

(51) Int. Cl.
*C07D 311/02* (2006.01)
(52) U.S. Cl. .................................................. 549/288
(58) Field of Classification Search ............... 549/288
See application file for complete search history.

(56) References Cited

OTHER PUBLICATIONS

Seyedsayadost et al. Organic Letters, 2010, 12 (4), 716-719.*
Munakata et al. Yakugaku Zasshi (1981), 101(2), 132-7.*
Antosz, F.J, D. B. Nelson, D. L. Herald, Jr., M. E. Munk, J. Am. Chem. Soc. 1970, 92, 4933.
Awakawa, T, K. Yokota, N. Funa, F. Doi, N. Mori, H. Watanabe, S. Horinouchi, Chem. Biol. 2009, 16, 613.
Barrett, A. R., Y. Kang, K. S. Inamasu, M. S. Son, J. M. Vukovich, and T. T. Hoang. 2008. Genetic tools for allelic replacement in *Burkholderia* species. Appl. Environ. Microbiol. 74:4498-508.
Barrett, A.J., M. A. Brown, Biochem. J. 1990, 271, 701.
Blasiak, L. C., F. H. Vaillancourt, C. T. Walsh, C. L. Drennan, Nature 2006, 440, 368.
Brett, P.J.; Deshazer, D.; Woods, D.E. Epidemiol. Infect. 1997, 118, 137.
Burkholder, P. R., and N. H. Giles. 1947. Induced biochemical mutations in *Bacillus subtilis*. Amer. J. Bot. 34.
Cardona, S. T., and M. A. Valvano. 2005. An expression vector containing a rhamnoseinducible promoter provides tightly regulated gene expression in *Burkholderia cenocepacia*. Plasmid 54:219-28.
Chandler, J.R., B. A. Duerkop, A. Hinz, T. E. West, J. P. Herman, M. E. Churchill, S. J. Skerrett, E. P. Greenberg, J. Bacteriol. 2009, 191, 5901.
Daniel, H., B. Spanier, G. Kottra, D. Weitz, Physiology 2006, 21, 93.
Dean, D. H., J. C. Orrego, K. W. Hutchison, and H. O. Halvorson. 1976. New temperate bacteriophage for *Bacillus subtilis*, rho 11. J. Virol. 20:509-19.
Duerkop, B. A., R. L. Ulrich, and E. P. Greenberg. 2007. Octanoyl-homoserine lactone is the cognate signal for *Burkholderia mallei* BmaRl-Bmal1 quorum sensing. J. Bacteriol. 189:5034-40.
Duerkop, B. A., J. P. Herman, R. L. Ulrich, M. E. Churchill, and E. P. Greenberg. 2008. The *Burkholderia mallei* BmaR3-Bmal3 quorum-sensing system produces and responds to N-3-hydroxy-octanoyl homoserine lactone. J. Bacteriol. 190:5137-41.
Duerkop, B. A., J. Varga, J. R. Chandler, S. B. Peterson, J. P. Herman, M. E. Churchill, M. R. Parsek, W. C. Nierman, E. P. Greenberg, J. Bacteriol. 2009, 191, 3909.
Enos-Berlage, J. L.; McCarter, L. L. J. Bacteriol. 2000, 182, 5513.
Farinha, M. A., and A. M. Kropinski. 1990. Construction of broad-host-range plasmid vectors for easy visible selection and analysis of promoters. J. Bacteriol. 172:3496-99.
Felnagle, E. A., E. E. Jackson, Y. A. Chan, A. M. Podevels, A. D. Berti, M. D. McMahon, and M. G. Thomas. 2008. Nonribosomal peptide synthetases involved in the production of medically relevant natural products. Mol. Pharm. 5:191-211.
Fischbach, M. A., and C. T. Walsh. 2006. Assembly-line enzymology for polyketide and nonribosomal peptide antibiotics: logic, machinery, and mechanisms. Chem Rev 106:3468-96.
Fischbach, M. A., J. Clardy, Nat. Chem. Biol. 2007, 3, 353.
Fujii, I., A. Watanabe, U. Sankawa, Y. Ebizuka, Chem. Biol. 2001, 8, 189.
Fujii, Y. Ikai, H. Oka, M. Suzuki, K. Harada, Anal. Chem. 1997, 69, 5146.
Galonic, D.P., E. W. Barr, C. T. Walsh, J. M. Bollinger, Jr., C. Krebs, Nat. Chem. Biol. 2007, 3, 113.
Gill, S. R.; Fouts, D. E.; Archer, G. L.; Mongodin, E. F.; Deboy, R. T.; Ravel, J.; Paulsen, I. T.; Kolonay, J. F.; Brinkac, L.; Beanan, M.; Dodson, R. J.; Daugherty, S. C.; Madupu, R.; Angiuoli, S. V.; Durkin, A. S.; Haft, D. H.; Vamathevan, J.; Khouri, H.; Utterback, T.; Lee, C.; Dimitrov, G.; Jiang, L.; Qin, H.; Weidman, J.; Tran, K.; Kang, K.; Hance, I. R.; Nelson, K. E.; Fraser, C. M. J. Bacteriol. 2005, 187, 2426.
Gould, T. A., J. Herman, J. Krank, R. C. Murphy, and M. E. Churchill. 2006. Specificity of acyl-homoserine lactone synthases examined by mass spectrometry. J. Bacteriol. 188:773-83.
M. Hori, K. Suzukake, C. Ishikawa, J. Antibiotics 1981, 34, 465.
Jorgensen, J. H., J. D. Turnidge, and J. A. Washington. 1999. 7th ed. Antibacterial susceptibility tests: Dilution and disc diffusion methods. Manual of clinical microbiology 7th ed. ASM Press. 1526-1543, Washington, D.C.
Keating, T. A., and C. T. Walsh. 1999. Initiation, elongation, and termination strategies in polyketide and polypeptide antibiotic biosynthesis. Curr. Opin. Chem. Biol. 3:598-606.
Keatinge-Clay, A. T., R. M. Stroud, Structure 2006, 14, 737.
Krebs, C., D. Galonic Fujimori, C. T. Walsh, J. M. Bollinger, Jr., Acc. Chem. Res. 2007, 40, 484.

(Continued)

*Primary Examiner* — Nizal Chandrakumar
(74) *Attorney, Agent, or Firm* — Perkins Coie LLP

(57) ABSTRACT

The present inventions are directed to a novel bactobolin analog bactobolin D. The present inventions also are directed to a method of producing a composition comprising at least one bactobolin analog using a bacteria strain comprising a bacterial cell comprising the biosynthetic locus of the bactobolin analog in *Burkholderia thailandensis* (bta cluster) or a homolog structure (at least 95% sequence identity) thereof, and further isolation and purification of the bactobolin analog. For example, the bacterial strain can be a wild type bacterial strain such as a *Burkholderia* strain comprising a bta cluster (e.g. *Burkholderia thailandensis* (e.g. E264, Bt4, and TXDOH) and *Burkholderia pseudomallei* (e.g. K96243, 1106a, and 1106b).

1 Claim, 10 Drawing Sheets

OTHER PUBLICATIONS

Figure 1:
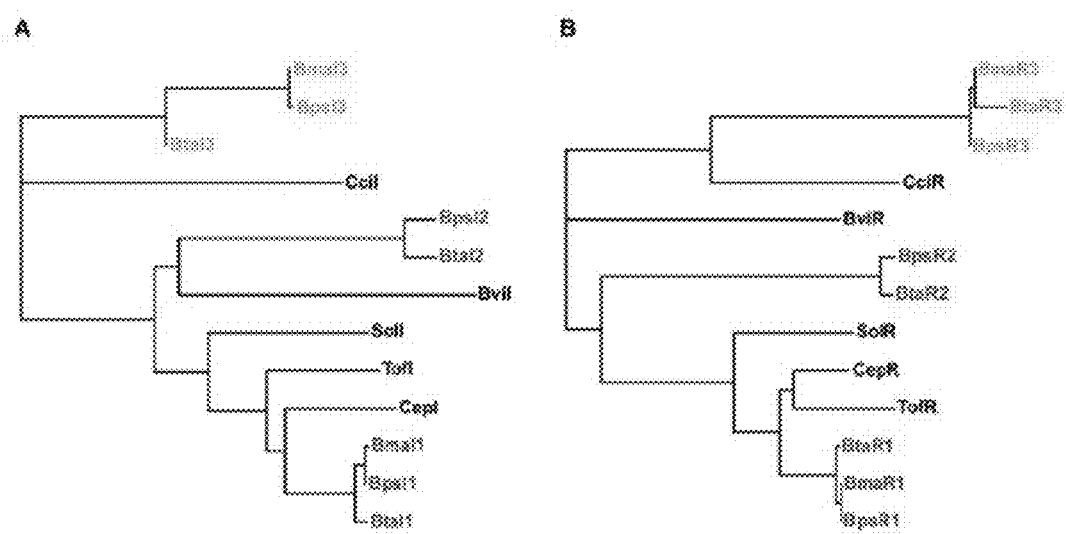

Kondo, S., Y. Horiuchi, M. Hamada, T. Takeuchi, H. Umezawa, J. Antibiotics 1979, 32, 1071.

Lewinson, O., J. Adler, N. Sigal, and E. Sibi. 2006. Promiscuity in multidrug recognition and transport: the bacterial MFS Mdr transporters. Mol Microbiol 61 :277-84.

Llano-Sotelo, B., E. F. Azucena, Jr., L. P. Kotra, S. Mobashery, and C. S. Chow. 2002. Aminoglycosides modified by resistance enzymes display diminished binding to the bacterial ribosomal aminoacyl-tRNA site. Chem. Biol. 9:455-63.

Neidig, M. L., et al., J. Am. Chem. Soc. 2007, 129, 14224.

Newman, J. R., and C. Fuqua. 1999. Broad-host-range expression vectors that carry the L-arabinose-inducible *Escherichia coli* araBAD promoter and the araC regulator. Gene 227: 197-203.

Paulsen, I. T.; Banerjei, L.; Myers, G. S.; Nelson, K. E.; Seshadri, R.; Read, T. D.; Fouts, D. E.; Eisen, J. A.; Gill, S. R.; Heidelberg, J. F.; Tettelin, H.; Dodson, R. J.; Umayam, L.; Brinkac, L.; Beanan, M.; Daugherty, S.; DeBoy, R. T.; Durkin, S.; Kolonay, J.; Madupu, R.; Nelson, W.; Vamathevan, J.; Tran, B.; Upton, J.; Hansen, T.; Shetty, J.; Khouri, H.; Utterback, T.; Radune, D.; Ketchum, K. A.; Dougherty, B. A.; Fraser, C. M. Science 2003, 299, 2071.

Railing, G., S. Bodrug, and T. Linn. 1985. Growth rate-dependent regulation of RNA polymerase synthesis in *Escherichia coli*. Mol. Gen. Genet. 201 :379-86.

Schaefer, A. L., B. L. Hanzelka, M. R. Parsek, and E. P. Greenberg. 2000. Detection, purification, and structural elucidation of the acylhomoserine lactone inducer of *Vibrio fischeri* luminescence and other related molecules. Methods Enzymol. 305:288-301.

Shaw, P. D., G. Ping, S. L. Daly, C. Cha, J. E. Cronan, Jr., K. L. Rinehart, and S. K. Farrand. 1997. Detecting and characterizing N-acyl-homoserine lactone signal molecules by thin-layer chromatography. Proc. Natl. Acad. Sci. U S A 94:6036-41.

Song, Y., C. Xie, Y. M. Ong, Y. H. Gan, and K. L. Chua. 2005. The BpsIR quorum-sensing system of *Burkholderia pseudomallei*. J. Bacteriol. 187: 785-90.

Strieter, E. R., F. H. Vaillancourt, C. T. Walsh, Biochemistry 2007, 46, 7549.

Tang, L., Y. J. Yoon, C.-Y. Choi, C. R. Hutchinson, Gene 1998, 216, 255.

Ullrich, M., and C. L. Bender. 1994. The biosynthetic gene cluster for coronamic acid, an ethylcyclopropyl amino acid, contains genes homologous to amino acid-activating enzymes and thioesterases. J. Bacteriol. 176:7574-86.

Vaillancourt, F. H., E. Yeh, D. A. Vosburg, S. E. O'Connor, and C. T. Walsh. 2005. Cryptic chlorination by a non-haem iron enzyme during cyclopropyl amino acid biosynthesis. Nature 436: 1191-4.

Vetting, M. W., S. d. C. LP, M. Yu, S. S. Hegde, S. Magnet, S. L. Roderick, and J. S. Blanchard. 2005. Structure and functions of the GNAT superfamily of acetyltransferases. Arch. Biochem. Biophys. 433:212-26.

Vimr, E. R., L. Green, C. G. Miller, J. Bacteriol. 1983, 153, 1259.

Wuthiekanun,V., M. D. Smith, D.A. Dance, A. L. Walsh, T. L. Pitt, and N. J. White. 1996. Biochemical characteristics of clinical and environmental isolates of *Burkholderia pseudomallei*. J. Med. Microbiol. 45:408-12.

Zhang, Z., S. Schwartz, L. Wagner, and W. Miller. 2000. A greedy algorithm for aligning DNA sequences. J. Comput. Biol. 7203-14.

* cited by examiner

A

B

US 8,222,434 B1

BACTOBOLIN ANALOG AND SYNTHESIS METHOD THEREOF

PRIORITY CLAIM

The present application claims priority to U.S. Provisional Application 61/166,729, filed Apr. 4, 2009, U.S. Provisional Application 61/168,589, filed Apr. 11, 2009, and U.S. Provisional Application 61/260,806, filed Nov. 12, 2009 which are incorporated herein by reference in their entirety.

STATEMENT REGARDING FEDERALLY SPONSORED RESEARCH OR DEVELOPMENT

The invention was made with Government support under Grant number U54A1057141, Grant number T32 GM07270 and Grant number GM086258 awarded by the National Institutes of Health. The U.S. Government has certain rights in this invention.

FIELD OF THE INVENTION

This invention relates to the field of antibiotic compound and compositions and synthesis thereof.

BACKGROUND OF THE INVENTION

Bactobolin analogs (e.g. bactobolin, bactobolin B and bactobolin C) are known antibiotics.[1] However, due to their complex chemical structures, it is difficult to produce bactobolin analogs in high volume. It is also challenging to synthesize novel analogs of bactobolin for more desirable properties. Therefore, a need exists to prepare novel bactobolin analogs and to produce bactobolin analogs in greater amount.

SUMMARY OF THE INVENTION

One aspect of the invention relates to a novel bactobolin analog bactobolin D.

Another aspect of the invention relates to a method of preparing a composition comprising a bactobolin analog (e.g. bactobolin, bactobolin B, bactobolin C and bactobolin D) using a bacteria strain comprising a bacterial cell comprising the biosynthetic locus of the bactobolin analog in *Burkholderia thailandensis* (bta cluster) or a homolog structure (at least 95% sequence identity) thereof. In certain embodiments, the bacterial strain is a wild type bacterial strain such as a *Burkholderia* strain comprising a bta cluster (e.g. *Burkholderia thailandensis* (e.g. E264, Bt4, and TXDOH) and *Burkholderia pseudomallei* (e.g. K96243, 1106a, and 1106b). In certain embodiments, the bacterial strain comprises a genetically-engineered bacterial cell comprising an inserted bta cluster.

In certain embodiments, the bactobolin analog(s) is (are) further isolated and purified.

Another aspect of the invention relates to a method of preparing a bactobolin analog by mutating the bta cluster in *Burkholderia thailandensis*.

Another aspect of the invention relates to a method of preparing a bactobolin analog using a bacteria strain comprising a bacterial cell comprising a mutant bta cluster or a homolog structure thereof.

BRIEF DESCRIPTION OF THE SEVERAL VIEWS OF THE DRAWINGS AND TABLES

FIG. 1. Dendrograms showing relatedness of *Burkholderia thailandensis* (Bta), *Burkholderia pseudomallei* (Bps) and *Burkholderia mallei* (Bma) LuxR and LuxI homologs to each other and to homologs from other species of β-*Profeobacteria*. The amino acid sequences were obtained from publicly available genome sequence data bases. Geneious 4.0.2 was used to produce the dendrograms with the multiple sequence alignment tool. Bvi, *B. vietnamiensis*; Cep, *B. cenocepacia*; Cci, *B. cenocepacia*; T of, *B. glumae*; Sol, *R. solanacearum*.

Figure 2:
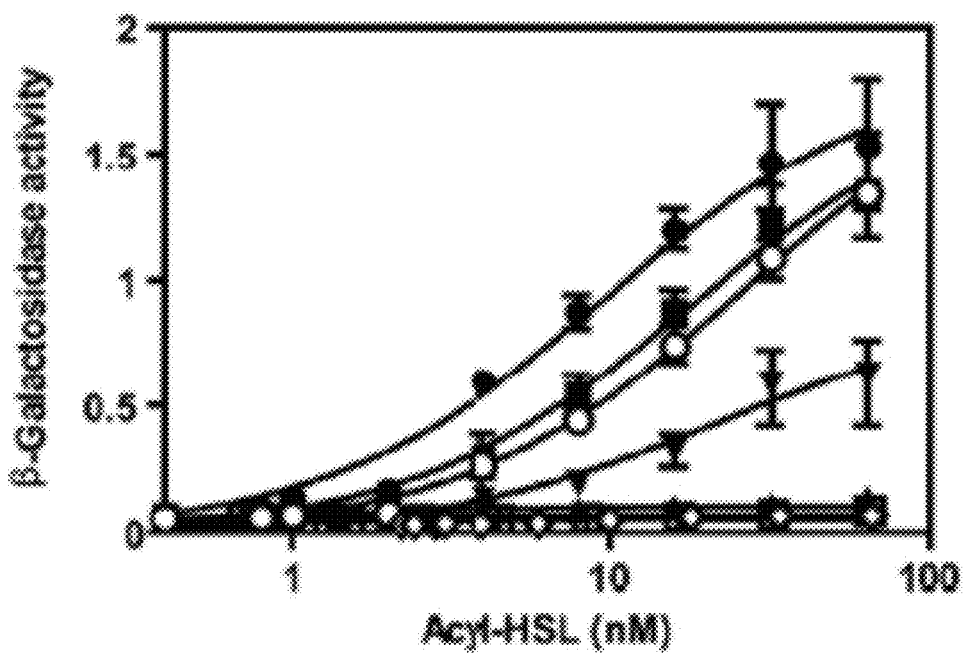
Figure 2:
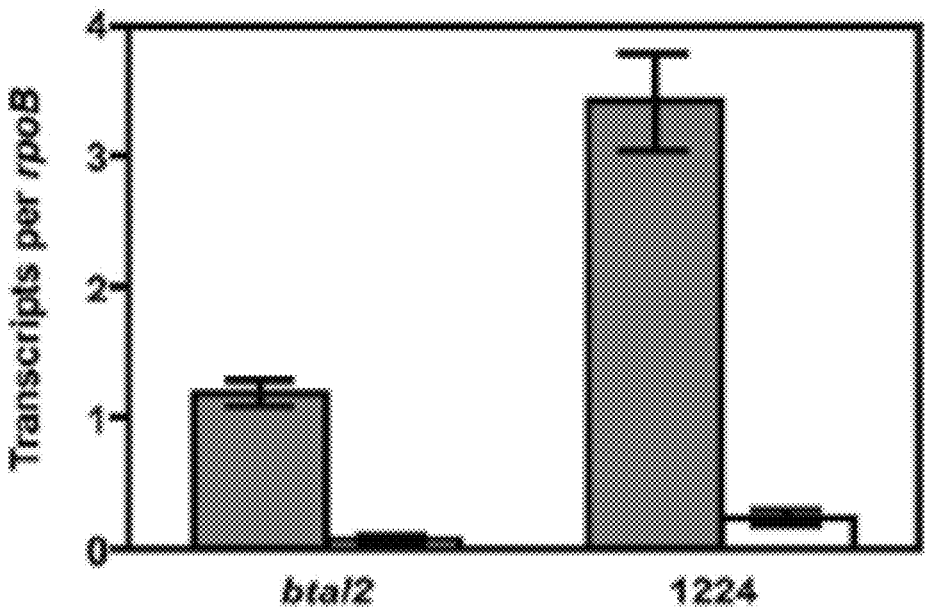

FIG. 2. Transcriptional activation of genes in the btaI2 operon requires 3OHC10-HSL or 3OHC8-HSL, and BtaR2. (A) Acyl-HSL dose responses of the btaI2 promoter in *E. coli* containing a BtaR2 expression vector (pJNR2) and a btaI2-lacZ fusion vector (p12P50). The following acyl-HSLs were tested: (■) 3OHC10-HSL, (●) 3OHC8-HSL, (□) 3OHC6-HSL, (▼) C12-HSL, (○) C10-HSL, (▲) C8-HSL. (◇) indicates the 3OHC10-HSL response in the absence of BtaR2. Error bars represent the range of three independent experiments. P-galactosidase activity is given as millions of relative light units. (B) Relative transcript levels of btaI2 and the downstream gene BTH-111224 from wild-type *B. thailandensis* (grey bars) and the BtaR2 mutant strain JBT108 (white bars). Error bars represent the range of two independent experiments assayed in triplicate.

Figure 3:
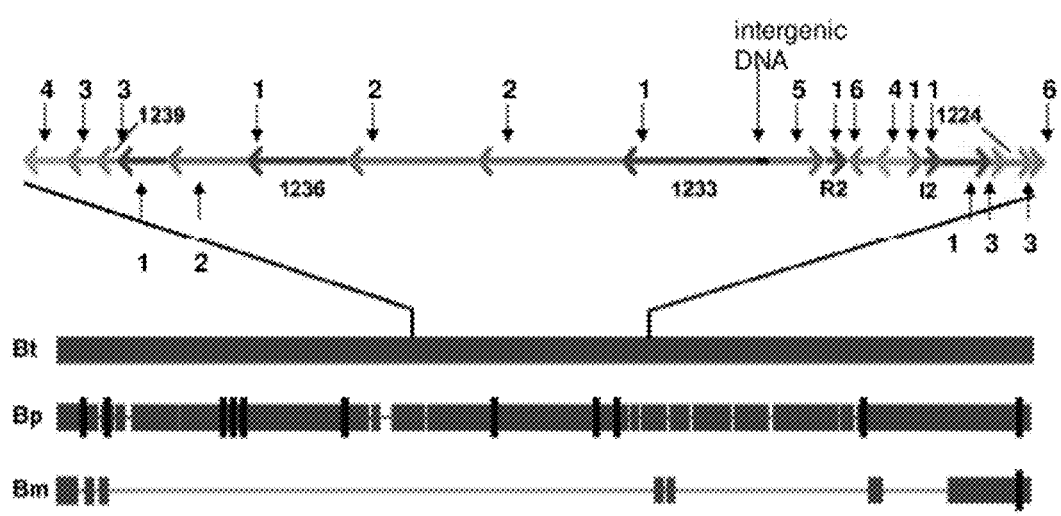

FIG. 3. Organization of the *B. thailandensis* btaR2-btaI2 genomic region. Map of the genes in the immediate vicinity of btaR2 and btaI2. The btaR2 and btaI2 genes are separated by three open reading frames encompassing about 3.3-kb of DNA. btaI2 resides in a predicted five-gene operon that contains open reading frames annotated to function in antibiotic synthesis. btaR2 is 3-kb upstream of a cluster containing putative antibiotic biosynthesis genes. The arrows labeled R2 and I2 represent btaR2 and btaI2, respectively. Arrows labeled 1 are annotated as NRPS genes, arrows labeled 2 indicate PKS genes, arrows labeled 3 are potential accessory antibiotic synthesis genes, arrows labeled 4 are putative transport genes, arrow labeled 5 is a metallopeptidase, and arrows labeled 6 indicate genes of unknown function. The black lines between coding regions represent intergenic DNA. Grey bars represent the btaR2-btaI2 genomic region and the flanking DNA which is conserved in *B. pseudomallei* and mostly absent from the *B. mallei* chromosome. The genomic sequences were obtained from the publicly available genome sequences of *B. thailandensis* strain E264, *B. pseudomallei* strain K96243 and *B. mallei* strain ATCC 23344. Alignments were generated using the nucleotide BLAST algorithm.[2] The *B. thailandensis* E264 genomic sequence was used as the reference sequence. A solid purple bar indicates congruence in nucleic acid sequence, the amino acid sequences within these regions share >90% identity. Vertical black bars represent nucleic acid sequence of dissimilarity and gaps between purple bars are missing sequences. The arrows representing btaR2, btaI2 and their surrounding genes are drawn to scale.

Figure 4:
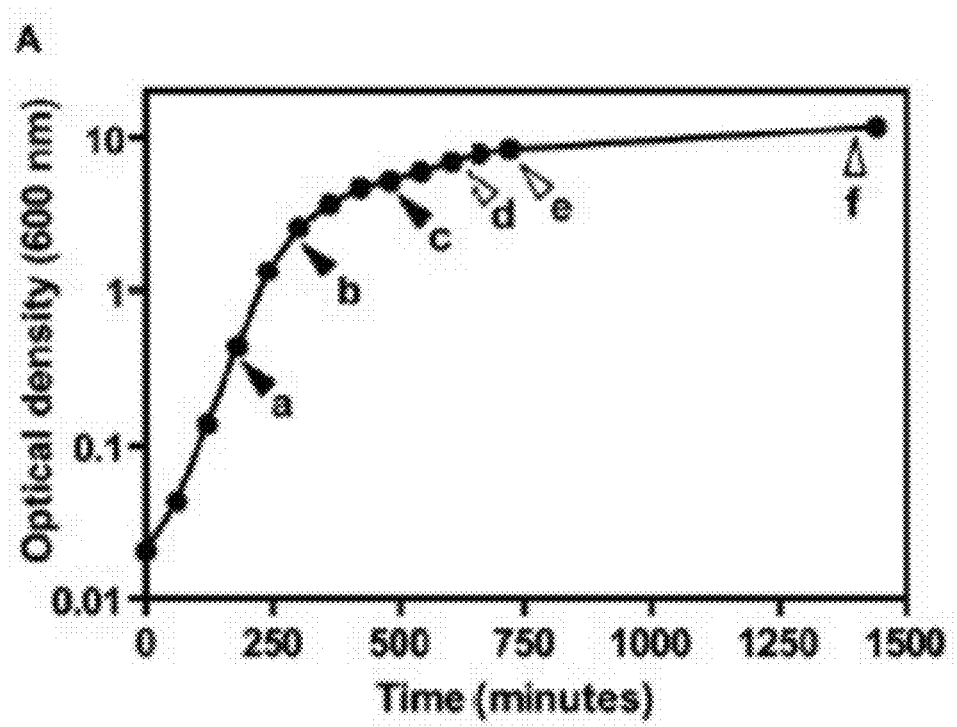
Figure 4:
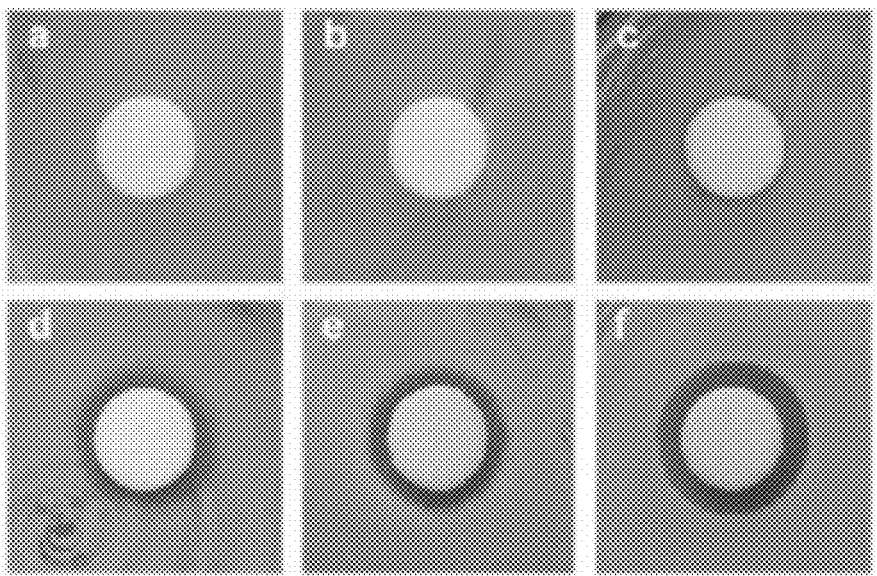

FIG. 4. Sensitivity of *B. subtilis* to a substance in *B. thailandensis* stationary phase culture fluid. (A) Growth curve of the wild-type *B. thailandensis* strain E264. Arrows marked a-f indicate points where culture fluid was taken for the analysis shown in B. (B) Antibiotic sensitivity assays. Paper diffusion discs were saturated with fluid from a *B. thailandensis* E264 culture at the indicated points (a-f in A) and placed on lawns of *B. subtilis*. A zone of clearing around a diffusion disc indicates the region where *B. subtilis* growth was inhibited. Open arrows in A indicate points in growth where antibiotic was produced.

Figure 5:
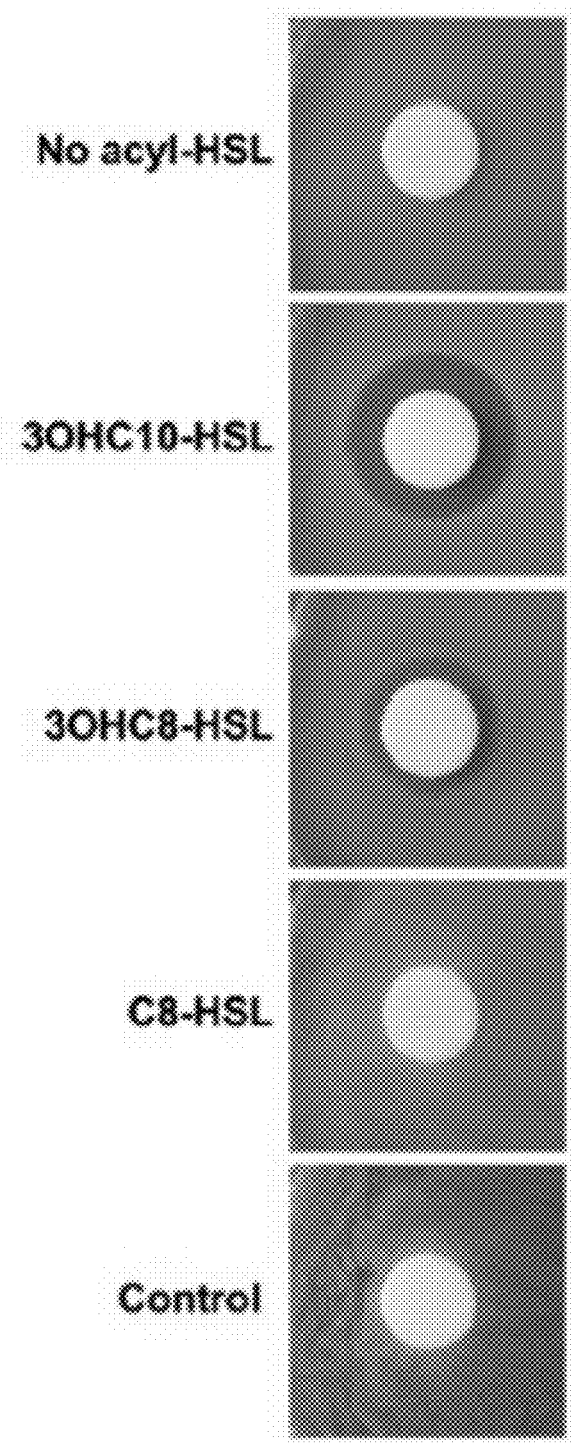

FIG. 5. A *Burkholderia thailandensis* acyl-HSL synthesis mutant requires exogenous 3OHC8-HSL or 3OHC10-HSL for antibiotic production. Diffusion disc assays with fluid from a stationary phase culture of the btaI1, btaI2, btaI3 triple mutant JBT112 grown without added signal, or with 2 µM 3OHC8-HSL or 3OHC10-HSL as indicated. Growth on the *B. subtilis* lawn is inhibited by culture fluid from 3OHC10-HSL or 3OHC8-HSL grown *Burkholderia thailandensis* JBT112, but not by JBT112 grown without an added acyl-HSL or in the presence of 2 µM C8-HSL. The bottom panel shows a diffusion disc that had been soaked in sterile medium containing 2 µM 3OHC10-HSL. This control shows that 3OHC10-HSL itself is not an antimicrobial molecule.

Figure 6:
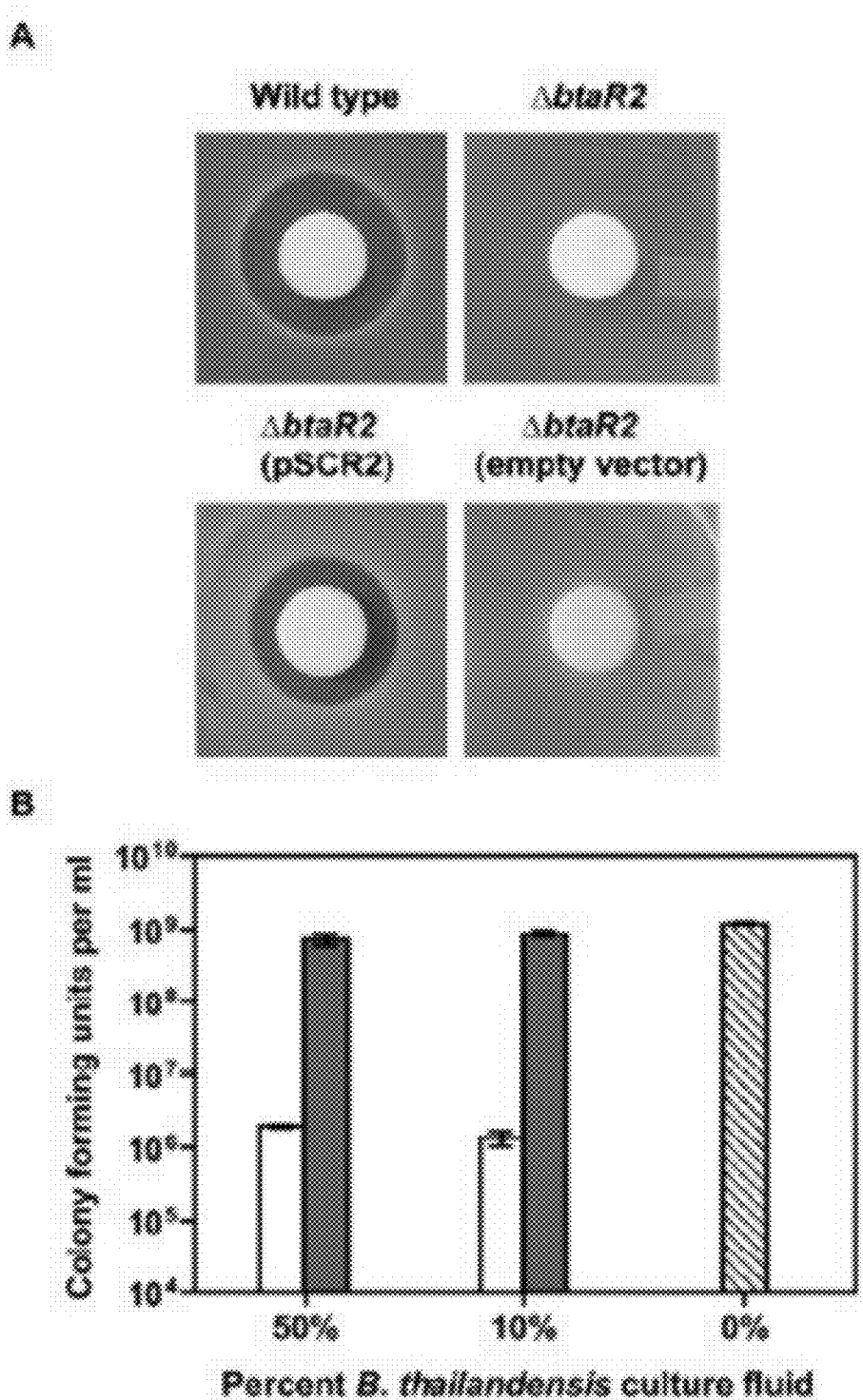
Figure 7:
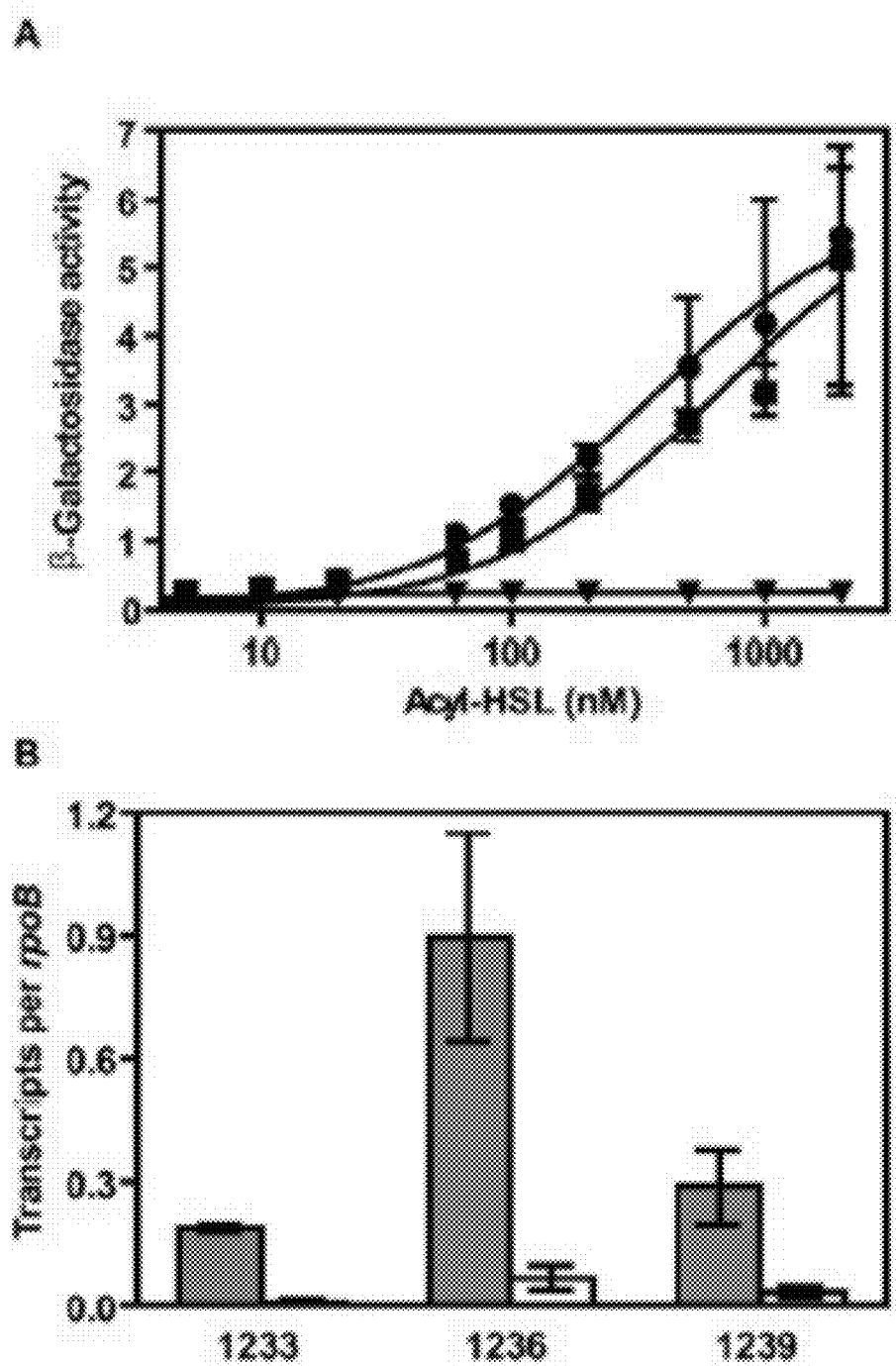

FIG. 6. *Burkholderia thailandensis* BtaR2 is required for antibiotic production. (A) A diffusion disc experiment showing antibiotic activity of fluid from a *Burkholderia thailandensis* E264 (wild-type) stationary phase culture, JBTI 08 (bfaR2 mutant) stationary phase culture, and JBT108 complemented with the BtaR2 expression plasmid pSCR2. The control is strain JBT108 carrying the empty vector pSCrhaB2. *B. subtilis* was used as the indicator strain. (B) Influence of *Burkholderia thailandensis* culture FIG. 7. Dependence of BTH_II1233, 1236, and 1239 transcription on the BtaI2-BtaR2 quorum sensing system. (A) Acyl-HSL dose responses of the BTH_II1233-lacZ fusion on pQF1233 and btaR2 on pJNR2 in *E. coli*; (■) 3OHC10-HSL, (●) 3OHC8-HSL. The BTH_II1233-lacZ response to 3OHC10-HSL in *E. coli* without a BtaR2 expression vector is also shown (▼). The error bars are the range of three independent experiments. P-galactosidase activity is given as millions of relative light units. (B) Relative transcript levels of BTH_II1233 and the downstream genes BTH_II1236 and BTH_II1239 from wild-type *Burkholderia thailandensis* E264 (grey bars) and the btaR2 mutant strain JBT102 (white bars). Values represent the range of two independent experiments assayed in triplicate.

Figure 8:
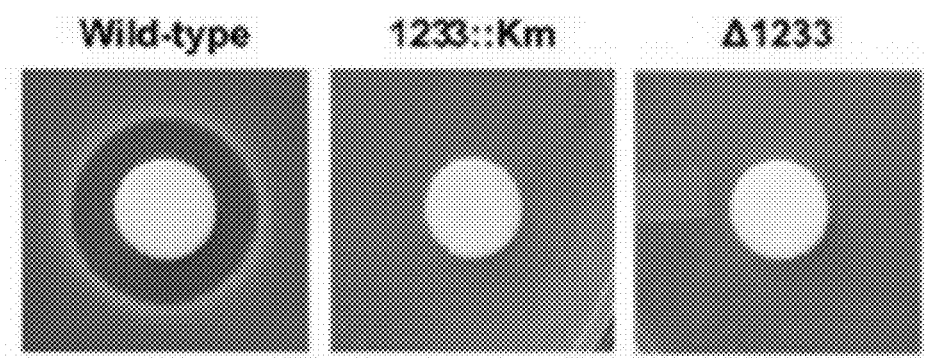
Figure 8:
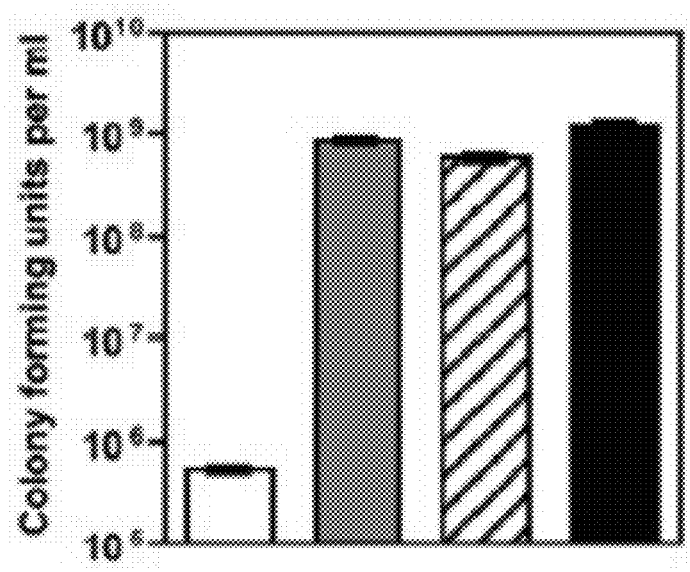

FIG. 8. BTH_II1233 mutants do not produce antibiotic. (A) Diffusion disc assays with fluid from stationary phase cultures of *Burkholderia thailandensis* E264 (wild type), the BTH_II1233 kanamycin insertion mutant BD909 and the in-frame deletion mutant BD20. The tester bacterium was *B. subtilis*. (B) Influence of *Burkholderia thailandensis* culture fluid (10% vol/vol) on growth of *B. subtilis* in broth assessed by colony counting. The *Burkholderia thailandensis* wild type strain E264 is indicated by the white bar. The 1233-insertion mutant, BD909, and the 1233 in-frame deletion mutant, BD20, are indicated by the grey and dashed bar, respectively. For reference a control culture with no added *Burkholderia thailandensis* culture fluid is shown (black bar).

Figure 9:
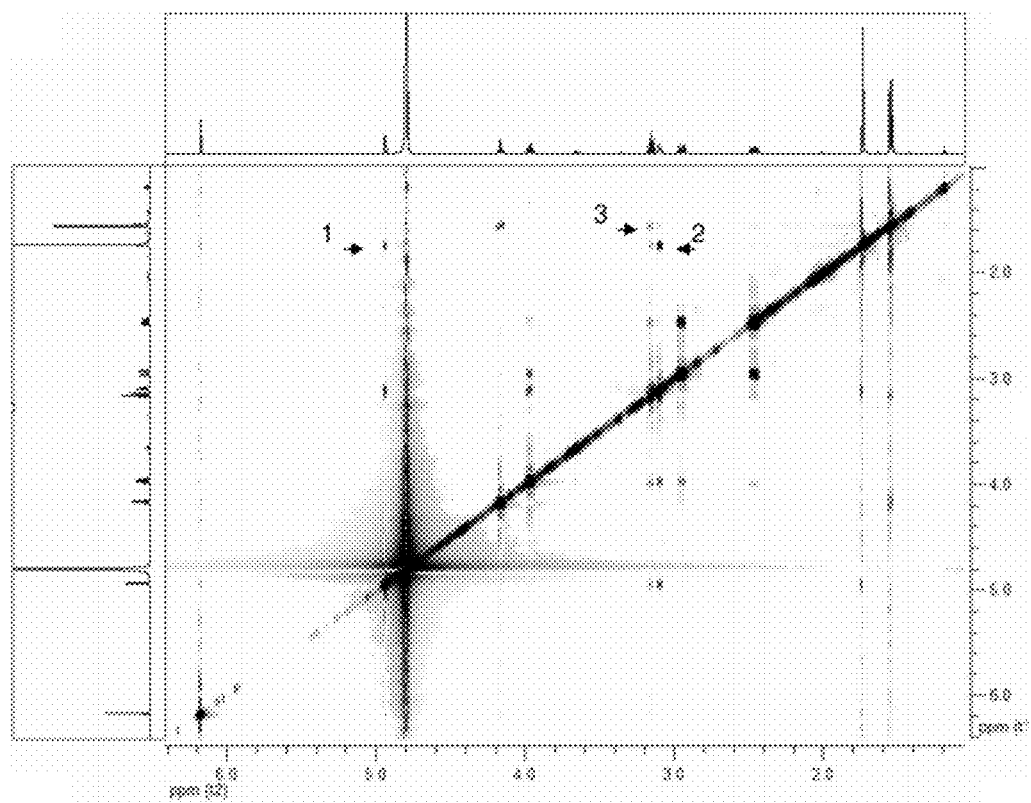

FIG. 9. ROESY spectrum of bactobolin A in $H_2O$ (+0.2% TFA). Arrow 1 indicates a ROESY correlation between H4 and H3b correlation; arrow 2 indicates a ROESY correlation between H3b and H10; and arrow 3 indicates a ROESY correlation between H5 and H4'.

Figure 10:
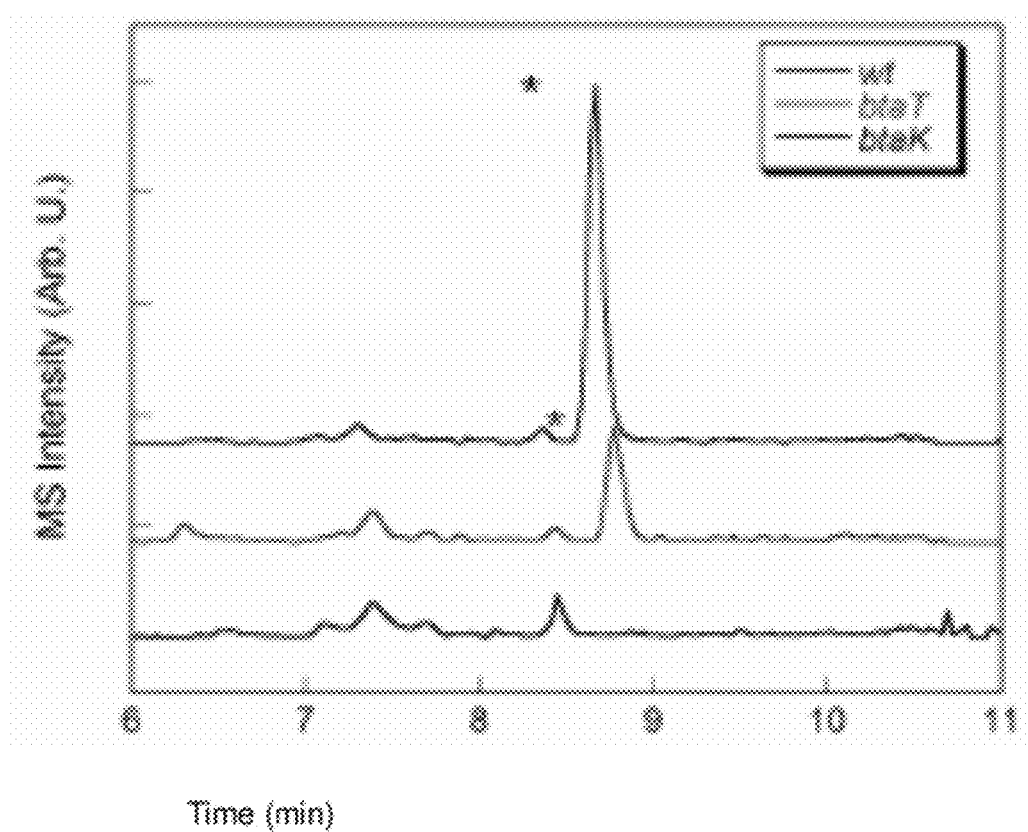

FIG. 10. Ion-extracted LC-MS trace of the culture supernatants of wt *Burkholderia thailandensis* vs those of the btaT and btaK deletion mutants after 24 h of growth. The starred peaks correspond to bactobolin B. The volume analyzed for the btaK/btaT mutants was 3-fold that of wt.

DETAILED DESCRIPTION OF THE INVENTION

One aspect of the invention relates to bactobolin D having a chemical structure of the following Structure I:

Structure 1 wherein $R^1$ is H and $R^2$ is L-Ala.

Another aspect of the invention relates to a method of preparing a composition comprising a bactobolin analog in high volume using a *Burkholderia* strain that comprises the biosynthetic locus of the bactobolin analog in *Burkholderia thailandensis* (bta cluster) or a homolog structure (at least 95% sequence identity) thereof, which comprises the following steps 1-3:
  1) providing a stationary phase culture of the *Burkholderia* strain;
  2) removing the cells from the cell culture; and
  3) filtering the culture fluid to obtain a composition comprising the bactobolin analog.

As used herein, the term "bactobolin analog" means a compound comprising a chemical structure of Structure I, wherein:
  $R^1$ is selected from the group consisting of H and OH; and
  $R^2$ is selected from the group consisting of H and L-Ala.

Examples of bactobolin analog include, without limitation, bactobolin (Structure I, wherein $R^1$ is OH and $R^2$ is H), bactobolin B (Structure I, wherein $R^1$ is OH and $R^2$ is L-Ala), bactobolin C (Structure I, wherein $R^1$ and $R^2$ are both H) and bactobolin D.

Examples of bacterial strains comprising a bta cluster include, without limitation, *Burkholderia thailandensis* (*B. thailandensis*, e.g. *B. thailandensis* E264, *B. thailandensis* Bt4, and *B. thailandensis* TXDOH) and *Burkholderia pseudomallei* (*B. pseudomallei*, e.g. *B. pseudomallei* K96243, *B. pseudomallei* 1106a, and *B. pseudomallei* 1106b).

In certain embodiments, a stationary phase culture of *B. thailandensis* was prepared by growing the bacteria in Luria-Bertani (LB) broth containing MOPS (50 mM, pH 7.0) at 37° C. until *B. thailandensis* reached late stationary phase ($OD_{600}$ 9-10).

Another aspect of the invention relates to a method of preparing a composition comprising a bactobolin analog using a bacteria strain comprising a bacterial cell comprising bta cluster or a homolog structure thereof, which comprises the following steps 1-4:
  1) inserting the bta cluster into a bacterial cell to provide a bacterial cell comprising the bta cluster;
  2) providing a stationary phase culture of the bacterial cell;
  3) removing the cells from the cell culture; and
  4) filtering the culture fluid to obtain a composition comprising the bactobolin analog.

In certain embodiments, the bactobolin analog is selected from the group consisting of bactobolin, bactobolin B, bactobolin C, and bactobolin D.

Examples of bacterial cell that can be used in the method of the present disclosure include, without limitation, *E. coli*.

Another aspect of the invention relates to a method of preparing a bactobolin analog in high volume using a

*Burkholderia* strain that comprises bta cluster or a homolog structure (at least 95% sequence identity) thereof, which comprises the following steps 1-5:
1) providing a stationary phase culture of the *Burkholderia* strain;
2) removing the cells from the cell culture;
3) filtering the culture fluid to obtain a composition comprising the bactobolin analog; and
4) isolating and purifying the bactobolin analog from the composition by activity-guided fractionation against *B. subtilis* 3610.

In certain embodiments, the bactobolin analog is selected from the group consisting of bactobolin, bactobolin B, bactobolin C, and bactobolin D.

In certain embodiments, the bacterial strain is a *B. thailandensis* strain (e.g. *B. thailandensis* E264, *B. thailandensis* Bt4, and *B. thailandensis* TXDOH) or a *B. pseudomallei* strain (e.g. *B. pseudomallei* K96243, *B. pseudomallei* 1106a, and *B. pseudomallei* 1106b).

Another aspect of the invention relates to a method of preparing a bactobolin analog using a bacteria strain comprising a bacterial cell comprising bta cluster or a homolog thereof, which comprises the following steps 1-4:
1) inserting the bta cluster into a bacterial cell to provide a bacterial cell comprising the bta cluster;
2) providing a stationary phase culture of the bacterial cell;
3) removing the cells from the cell culture;
4) filtering the culture fluid to obtain a composition comprising the bactobolin analog; and
5) isolating and purifying the bactobolin analog from the composition by activity-guided fractionation against *B. subtilis* 3610.

In certain embodiments, the bactobolin analog is selected from the group consisting of bactobolin, bactobolin B, bactobolin C, and bactobolin D.

Another aspect of the invention relates to a method of preparing a bactobolin analog by mutating the bta cluster in a *Burkholderia* strain, which comprises the following steps 1-5:
1) mutating one or more genes in the bta cluster of the *Burkholderia* strain cell;
2) providing a stationary phase culture of *B. thailandensis*;
3) removing the cells from the cell culture;
4) filtering the culture fluid to obtain a composition comprising the bactobolin analog; and
5) purifying the compound from the composition by activity-guided fractionation against *B. subtilis* 3610.

In certain embodiments, the bactobolin analog is selected from the group consisting of bactobolin, bactobolin B, bactobolin C, and bactobolin D.

In certain embodiments, a method comprises:
providing a mutant bta cluster;
inserting the mutant bta cluster into a bacterial cell;
providing a stationary phase culture comprising the bacterial cell; removing the cells from the cell culture; and
filtering the culture fluid to obtain a composition comprising at least one bactobolin analog.

Another aspect of the invention relates to a method of preparing a bactobolin analog by feeding a *Burkholderia* strain comprising the bta cluster alternative natural or unnatural amino acids, which comprises the following steps:
1) providing a stationary phase culture of the *Burkholderia* strain with alternative natural or unnatural amino acids;
2) removing the cells from the cell culture;
3) filtering the culture fluid to obtain a composition comprising the bactobolin analog; and
4) purifying the compound from the composition by activity-guided fractionation against *B. subtilis* 3610.

In certain embodiments, the bacterial strain is a *B. thailandensis* strain (e.g. *B. thailandensis* E264, *B. thailandensis* Bt4, and *B. thailandensis* TXDOH) or a *B. pseudomallei* strain (e.g. *B. pseudomallei* K96243, *B. pseudomallei* 1106a, and *B. pseudomallei* 1106b).

As used herein, the term "bma genes" means luxR and luxI homologs in *Burkholderia mallei* (*B. mallei*). The term "bps genes" means luxR and luxI homologs in *Burkholderia pseudomallei* (*B. pseudomallei*). The term "bta genes" means luxR and luxI homologs in *Burkholderia thailandensis* (*B. thailandensis*). The term "bta cluster" means a DNA sequence comprising the genes that are required for the biosynthetic locus of the composition comprising at least one bactobolin analog of *B. thailandensis*. In certain embodiments, a bta cluster comprises genes selected from the group consisting of btaK, btaN, btaO, btaM, btaL, btaI2, btaR2, BtaD, BtaC, BtaE, BtaA, BtaU and BtaH, and any combination thereof.

As used herein, btaK gene refers to 1233, btaT refers to 1241, btaL refers to 1234, btaP refers to 1238, btaB refers to 1223, and btaU refers to 1242 respectively on chromosome II

EXAMPLES

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Materials and Methods

A) Bacterial Culture Conditions.
The bacterial strains used in this study are listed in Table 1-A.

TABLE 1-A

Bacterial strains.

| Strain | Relevant properties | Reference or source |
|---|---|---|
| *B. thailandensis* | | |
| E264 | Wild-type strain | (4) |
| JBT102 | btaI2 mutant of E264 | Chandler at al., in preparation |
| JBT105 | btaI1, btaI3 double mutant of E264 | Chandler et al., in preparation |
| JBT108 | btaR2 mutant of E264 | Chandler et al., in preparation |
| JBT112 | btaI1, btaI2, btaI3 triple mutant of E264 | Chandler et al., in preparation |
| BD909 | BTH_II1233::Km insertion mutant of E284 | This study |
| BD20 | BTH_II1233 mutant of E264 | This study |

TABLE 1-A-continued

Bacterial strains.

| Strain | Relevant properties | Reference or source |
|---|---|---|
| *E. coli* | | |
| DH5α | F φ80lacZΔM15 Δ(lacZYA-argF) U169 hsdR17($r_k^-$, $m_k^+$) recA1 endA1 phoA supE44 thi-1 gyrA96 relA1 N | Invitrogen |
| MG4 | F N ilvG rfb-50 rph-1 recA Δ:argF-lacIPOZYA)205 | (47) |
| SM10 | thi thr leu tonA lacY supE recA:: RP4-2-Tc::Mu Km λpir | (54) |
| *B. subtilis* | | |
| 168 | Wild-type strain, trpC2 | (5) |
| 3610 | Wild-type strain, φ3T | (10) |
| *L. monocytogenes* | | |
| ATCC 15313 | Wild-type strain | American Type Culture Collection |
| *S. aureus* | | |
| MN8 | tstH+: clinical isolate from nonmenstrual toxic shock syndrome case | (50) |
| COL | Methicillin-resistant laboratory strain | (24) |
| *P. fluorescens* | | |
| 2-79 | Wild-type strain, Phz+, Rif+ | (66) |

Unless otherwise indicated all bacteria except *S. pyogenes* were grown in Luria-Bertani (LB) broth. *S. pyogenes* was grown on Todd Hewitt broth supplemented with 0.2% (wt/vol) yeast extract. The following antibiotics were used at the indicated concentrations for marker selection and for maintaining plasmids (per ml): 100 pg ampicillin, 15 pg gentamicin, 300 pg trimethoprim and 25 pg kanamycin for *E. coli*; 100 pg trimethoprim and 150 pg kanamycin for *B. thailandensis*. To induce arabinose promoter-controlled gene expression in *E. coli*, we used 0:2% (wt/vol) L-arabinose. We used 0.2% (wt/vol) L-rhamnose to activate the rhamnose responsive promoter in *B. thailandensis*. All bacteria were grown at 37° C. except *P. fluorescens* which was grown at 30° C.

B) Plasmids and Recombinant DNA Procedures.

The plasmids used in this study are listed in Table 1-B:

TABLE 1-B

Plasmids

| Plasmids | Relevant properties* | Reference or source |
|---|---|---|
| pJN105 | araC-$P_{araBAD}$ cloned into pBBR1MCS-5; GM$^r$ | (43) |
| pQF50 | Broad-host-range lacZ fusion vector: Ap$^r$ | (18) |
| pSCrhaB2 | rhaRS-$P_{rhaBAD}$, dhfr cloned into pBBR1MCS: Tp$^r$ | (6) |
| pJRC115 | Mobilizable suicide vector, Tp$^r$ | Chandler et al., in preparation |
| pGEM-T Easy:amrRAB-oprA::FRT-Km | pGEM-T Easy with Δ(amrRAB-oprA):: FRT-$P_{EM7}$-kam-FRT fragment; Ap$^r$ Km$^r$ | Mima and Schweizer, unpublished |
| pI2P50 | pQF50 containing a 244-bp fragment of the btaI2 promoter extending from +6 with respect to the translation start site to −238; Ap$^r$ | This study |
| pJNR2 | pJN105 containing the btaR2 gene; Gm$^r$ | This study |
| pSCR2 | pSCrhaB2 containing the btaR2 gene; Tp$^r$ | This study |
| pQF1233 | pQF50 containing a 422-bp fragment of the BTH_II1233 promoter extending from position +13 with respect to the translation start site to −409; Ap$^r$ | This study |
| pLARA1233 | pJRC115 with ΔBTH_II1233 extending from +13 with respect to the translational start site to +1060, Tp$^r$ | This study |
| pKM1233 | FRT-$P_{EM7}$-kam-FRT fragment from pGEM-T Easy:amrRAB-oprA:: FRT-Km cloned into pLARA1233, Ap$^r$ Km$^r$ | This study |
| pINF1233 | pJRC115 with ΔBTH_II1233 extending from +13 with respect to the translational start site to +4313, Tp$^r$ | This study |

*$P_{araBAD}$, $P_{rhaBAD}$, and $P_{EM7}$, dhfr are the arabinose inducible promoter, the rhamnose inducible promoter, the synthetic bacterial EM7 promoter, and dihyrofolate reductase Oligonucleotides were purchased from Integrated DNA technologies (Coralville, Iowa). *B. thailandensis* genomic DNA was purified by using a Gentra Puregene Cell Plus isolation kit (Qiagen, Valencia, Calif.). PCR fragments were amplified with the Failsafe™ PCR System and buffer J or K premix solution (Epicentre Biotechnologies, Madison, Wis.) or with an Expand Long Template kit (Roche Diagnostics, Pleasanton, Calif.). *B. thailandensis* genomic DNA was used as the template for all PCR reactions. Plasmid DNA was isolated by using a Qiaprep mini-spin kit and PCR fragments used for cloning were purified with a Qiaquick PCR gel extraction kit (Qiagen).

To create the BtaR2 expression vector pJNR2, the open reading frame of btaR2 (BTH-111231) from bp −18 to +705 relative to the predicted translational start site was PCR amplified. This procedure introduced PsfI and SacI restriction sites at the ends of the btaR2 fragment. The btaR2 PCR product was ligated to PsfI-SacI-digested pJNIO5, which carries the L-arabinose inducible promoter ($P_{BAD}$).[3] To generate the lacZ transcriptional fusion constructs pI2P50 and pQF1233, *B. thailandensis* DNA upstream of btaI2 (BTH_II1227) and BTH_II1233 was PCR amplified by using primer pairs that incorporated NcoI and HindIII restriction sites at the ends of the PCR products. These products were cloned into NcoI-HindIII-digested pQF50.[4] The btaI2::lacZ fusion extends from +6 to −238 in relation to the predicted translational start site. BTH_II1233::lacZ extends from +13 to −409 in reference to the predicted translational start site.

To regulate expression of BtaR2 in *B. thailandensis* it was necessary to place btaR2 under the control of an inducible promoter other than the L-arabinose promoter. This is because *B. thailandensis* is known to metabolize L-arabinose.[5] We chose the rhamnose inducible promoter because of its utility in other *Burkholderia* species.[6] We constructed the BtaR2 expression vector pSCR2 by incorporating a PCR-amplified btaR2-containing DNA fragment into NcoI-HindIII-digested pSCrhaB2.[6] above The suicide vector pJRC115 was used to deliver modified genes into the *B. thailandensis* genome by allelic replacement. The method used for mutant construction in *B. thailandensis* is similar to that described recently.[7] To create pLARA1233, overlap extension PCR was used to generate DNA fragments of approximately 1-kb that were homologous to sequences flanking the intended site of deletion in BTH_II1233. These products were mixed and a second step PCR was done to anneal and amplify the fragments. Amplification created an internal XbaI in the product. The resulting PCR product was digested with XmaI and HindIII and ligated to XmaI-HindIII digested pJRC115, to yield pLARA1233. pLARA1233 was digested with XbaI and ligated to a 1.2-kb DNA fragment from XbaI digested pGEM-T Easy; amrRAB-oprA::FRT-Krn, which contains a kanamycin resistance cassette, creating the marked suicide vector pKM1233. pINF1233 was made by ligating a 2-kb DNA fragment generated by overlap extension PCR and this product was digested and ligated to XbaI-HindIII digested pJRC115. To construct the BTH_II1233 kanamycin-insertion mutant strain BD909 and the unmarked BTH_II1233 deletion strain BD20, pKM1233 and pINF1233 were mobilized from *E. coli* SM10 into *B. thailandensis*. Trimethoprim-resistant transconjugants were identified and then counter-selected by a method similar to that described elsewhere.[7] PCR followed by DNA sequencing was used to confirm the mutations. The nucleic acid sequence coordinates of insertion and replacement during the construction of BD909 and BD20 can be found in Table 1-A.

C) LC/MS/MS Identification of acyl-HSLs.

Acyl-HSLs were isolated from 10-ml cultures ($OD_{600}$ of 4.0) of wild-type *B. thailandensis* and the indicated mutant strains. Cells were removed from the culture fluid by centrifugation and the culture fluid was sterilized by using a 0.2 µM filter (Millipore, Billerica, Mass.). For LC/MS/MS, 0.4 nmol of deuterated C6-HSL ($D_3$-C6-HSL) and deuterated C12-HSL ($D_3$-C12-HSL) were added to the filtered culture fluid, which was then extracted with two equal volumes of acidified ethyl acetate (0.1 ml/L glacial acetic acid) and dried to completion under a constant stream of nitrogen gas. This was followed by a solid phase extraction, suspension of the material in 50 µL of 5% MeOH. Ten µL of each sample was analyzed by LC/MS/MS as described elsewhere.[8] The relative abundance of acyl-HSLs in each sample was determined by integrating the area under the analyte peaks and comparing these values to those of $D_3$-C6-HSL and $D_3$-C12-HSL standard curves.[8] Relative abundance is a measurement of the ratio of the areas of the analyte and internal standard peaks to the ratio of the amount of analyte and internal standard in each sample.

D) Acyl-HSL Bioassays.

To measure the BtaR2 response to acyl-HSLs we used recombinant *E. coli* with a btaI2-lacZ fusion or a BTH_II1233-lacZ fusion. Bioassays were performed as described elsewhere.[9] Briefly, an overnight culture of *E. coli* MG4[10] containing pJNR2 and pI2P50 was used to inoculate fresh LB broth containing arabinose (starting $OD_{600}$ 0.05). When the $OD_{600}$ reached 0.7, 0.5 ml of culture was added to tubes containing dried C8-HSL, C10-HSL, C12-HSL, 3OHC6-HSL, 3OHC8-HSL, or 3OHC10-HSL as indicated. After 3 h with shaking at 37° C., 50 µL of chloroform was added to each tube and β-galactosidase activity was measured using a Tropix Galacto-Light Plus kit according to the manufacturer's recommendations (Applied Biosystems, Foster City, Calif.). *E. coli* MG4 carrying pJNR2 and pQF1233 was used to measure the regulation of the BTH_II1233 promoter by BtaR2. The protocol was identical to that described for *E. coli* MG4 containing pJNR2 and pI2P50 except that only 3OHC8-HSL and 3OHC10-HSL were tested as signals.

E) Real-Time PCR.

Wild-type *B. thailandensis* and the btaR2 mutant JBT108 were grown in 25 ml of LB broth supplemented with 2% glycerol and 25 mM MOPS pH 7.0. At an $OD_{600}$ of 2.7, 4 ml of culture was treated with RNA protect (Qiagen) and after centrifugation the resulting cell pellet was suspended in 200 µL of Tris-EDTA (10 mM Tris base and 1 mM EDTA, pH 8) containing 10 mg/ml of lysozyme. Total RNA was purified with an RNeasy spin purification kit (Qiagen). For quantitative real-time PCR (qRT-PCR), cDNA was generated from 2 µg of RNA by using al TaqMan kit (Applied Biosystems). Primers were designed to amplify 100-200-bp targets for use in qRT-PCR reactions. The qRT-PCR reactions used 2× SYBR green master mix (Applied Biosystems) with 40 cycles of 15 s at 95° C. followed by 60 s at 62° C. The qRT-PCR program ended with a dissociation curve that was used to verify that a single product was amplified in each reaction and that primer dimers did not form. $C_t$ values were obtained with a manual threshold setting of 0.2. Values were generated by the calculation $2^{(35-C)}{}_t$. Results are reported as the calculated transcript amount of a given gene per calculated rpoB transcript. Reported values show the averages and range of biological replicates assayed in triplicate.

F) Antimicrobial Susceptibility Testing.

To assess antimicrobial activity in *B. thailandensis* culture fluid we routinely used a diffusion disc assay.[11] *B. thailandensis* cultures were grown in LB broth containing MOPS (50 mM, pH 7.0) at 37° C. Colonies grown overnight on LB-agar plates were used as the starting inoculum. Unless otherwise indicated, when *B. thailandensis* cultures reached late stationary phase ($OD_{600}$ 9-10) the cells were removed by centrifugation and the culture fluid was filtered thorough a 0.45 µm membrane. Antibiotic assay discs (13 mm, Whatman, Florham Park, N.J.) were saturated with sterile culture fluid and deposited onto LB agar plates overlayed with 100 µl of a 1:10 dilution of an overnight culture of *B. subtilis* 168[12] or other bacterial species as indicated. The plates were incubated at 37° C. overnight.

To measure antimicrobial activity more precisely and to assess whether the activity was bacteriocidal or bacteriostatic we used the following assay: Fluid from 24 h *B. thailandensis* cultures grown in LB containing 50 mM MOPS (pH 7.0) at 37° C. was collected and filter-sterilized (0.45 µm-pore-size membrane). Early log phase *B. subtilis* 3610[13] cells were inoculated into the filtered *B. thailandensis* culture fluid diluted with fresh LB-MOPS broth (initial *B. subtilis* density was approximately $1 \times 10^6$~cells per ml). After 24 h with shaking at 37° C. *B. subtilis* cell density was determined by plate counting on LB agar.

Example 2

The Biosynthetic Locus of the Antibiotic in *B. Thailandensis* (bta Cluster) Comprises BtaR2 and BtaI2 Gene Pair as a Quorum Sensing Regulation System A) The btaI2 Gene Product Catalyzes the Synthesis of 3OHC8-HSL and 3OHC10-HSL.

Acyl-HSL detection often involves bioassays or bioassays coupled to thin-layer-chromatographic separation of acyl-HSLs.[14,15] These methods rely on a specific LuxR homolog for acyl-HSL detection and they are biased for specific acyl-HSLs. It is cumbersome to conduct a comprehensive, quantitative analysis of acyl-HSLs using bioassays. Thus, we employed liquid chromatography-electrospray ionization-tandem mass spectrometry (LC/MS/MS), which detects acyl-HSLs in a complex mixture with high sensitivity irrespective of acyl side chain length or substitution and directly measures the relative abundance of acyl-HSLs,[8] to analyze acyl-HSLs produced by *B. thailandensis*. We analyzed acyl-HSLs in ethyl acetate extracts of stationary phase ($OD_{600}$ 4) culture fluid from wild-type *B. thailandensis* and quorum sensing mutants lacking btaI2 (JBT102) or both btaI1 and btaI3 (JBT105). Wild-type *B. thailandensis* produced C8-HSL, 3OHC8-HSL, 3OHC10-HSL, and a small amount of N-3-hydroxy-dodecanoyl-HSL (3OHC12-HSL) (Table 2-A).

TABLE 2-A

Relative amounts of acyl-HSLs produced by wild type and quorum sensing mutant strains of *B. thailandensis*

Relative abundance of acyl-HSLs[a]

| Acyl-HSL | Wild type | ΔbtaR2 | ΔbtaI1, ΔbtaI3 |
|---|---|---|---|
| C8-HSL | 27.5 (0.2) | 54.6 (0.6) | n.d.[b] |
| 3OHC8-HSL | 11.0 (0.06) | 45.4 (0.6) | 12.6 (1.8) |
| 3OHC10-HSL | 57.6 (0.5) | n.d. | 87.4 (1.8) |
| 3OHC12-HSL | 3.9 (0.2) | n.d. | n.d. |

[a]Values are the average percentage of acy-HSLs from two independent cultures and the range is indicated in parentheses.
[b]None detected.

The btaI2 mutant produced C8-HSL and 3OHC8-HSL but it did not produce detectable levels of 3OHC10-HSL (Table 2-A). This analysis suggests that BtaI2 is responsible for synthesis of 3OHC10-HSL. The btaI1-btaI3 double mutant produced both 3OHC8-HSL and 3OHC10-HSL. Taken together the data indicate that in *B. thailandensis* BtaI2 produced 3OHC8-HSL and 3OHC10-HSL. C8-HSL appears to be produced by either BtaI1 or BtaI3. BtaI1, BtaI3 or both are also capable of producing significant amounts of 3OHC8-HSL. Consistent with this interpretation the closely related *B. mallei* and *B. pseudomallei* I1 synthases produce C8-HSL,[9,16] and the *B. mallei* BmaI3 synthesizes 3OHC8-HSL.[17]

B) BtaR2 Regulates btaI2 Transcription in Response to 3OHC8-HSL or 3OHC10-HSL.

It is common that luxI homologs are positively autoregulated by the acyl-HSL signal(s) produced by the proteins they encode and the transcription factor encoded by the adjacent luxR homolog,10 The btaR2 and btaI2 gene organization is unusual in that there is approximately 3.3-kb of DNA between these two genes and this intervening DNA contains three open reading frames. We hypothesized that btaR2 and btaI2 may represent a cognate pair of quorum sensing genes and that btaI2 transcription would be activated by BtaR2 in response to 3OHC8-HSL, 3OHC10-HSL, or both signals. To test our hypothesis we created a plasmid with a 244-bp DNA fragment containing the putative promoter region of btaI2 (from −238 to +6 of the predicted translational start site) fused to a promoterless lacZ. This plasmid was introduced into *E. coli* with or without an arabinose-inducible btaR2. Activation of btaI2-lacZ transcription required BtaR2 and either 3OHC8-HSL or 3OHC10-HSL (FIG. 2A). There was also a response to N-decanoyl-HSL (C10-HSL) or N-dodecanoyl-HSL (C12-HSL), neither of which was detected in *B. thailandensis* culture fluid. There was no detectable response to C8-HSL or several other acyl-HSLs tested.

To verify that btaI2 transcription is regulated by BtaR2 in *B. thailandensis* we measured the abundance of btaI2 mRNA in wild type and the btaR2 mutant strain JBTI08 by using quantitative real-time PCR (qRT-PCR). The btaI2 gene is the first of five genes in a putative operon residing on Chromosome II. The qRT-PCR analysis showed that transcript levels of btaI2 and a downstream gene (1224) were substantially higher in the wild type than they were in the btaR2 mutant (FIG. 2B).

C) The btaR2 and btaI2 Genes Reside Among a Cluster of Putative Antimicrobial Biosynthetic Genes Conserved in *B. Pseudomallei* but Absent in *B. Mallei.*

Three of the genes in the putative btaI2 operon are predicted to code for enzymes involved in the production of secondary metabolites (FIG. 3). The second gene codes for a protein with similarity to nonribosomal peptide synthetases (NRPSs). NRPSs are involved in the production of amino acid-derived secondary metabolites.[18] The third gene's product contains a domain similar to those found in NRPS enzymes and the fourth gene codes for a protein with identity to a *Pseudomonas syringae* halogenase involved in the synthesis of the phytotoxin coronatine.[19,20] There is a cluster of genes (1233-1241) on chromosome II, upstream of btaR2, that codes for several additional NRPS polypeptides and several modular polyketide synthases (PKSs). Polyketide synthases function by incorporating fatty acids into secondary metabolites.[18] Many secondary metabolites produced by NRPSs, PKSs, and hybrid NRPS-PKS enzymes are medically important antimicrobials, immunosuppressants, or anticancer molecules.[21,22] Furthermore, the cluster distal to btaR2 also harbors genes that may play a role in the immunity to and transport of antibiotics.[23,24,25] We hypothesize that *B. thailandensis* uses BtaR2—BtaI2 quorum sensing to control antibiotic production.

The btaI2 and btaR2 genes reside amid a large cluster of genes, many of which we suspect are involved in production of secondary metabolites (FIG. 3). The alignment in FIG. 3 shows that there is extensive identity over an approximately 120-kb R2-I2 region of the *B. thailandensis* and *B. pseudomallei* Chromosome II. This 120-kb region is completely absent in *B. mallei*. The genes flanking this region are conserved among all three species.

D) *B. Thailandensis* Produces an Antibiotic.

Because btaI2 and btaR2 are embedded in a chromosomal region with many genes annotated as coding for functions known to be involved in antibiotic synthesis, transport and immunity by other bacteria, we hypothesized that *B. thailandensis* produces an antibiotic and that antibiotic production may require BtaR2 and an acyl-HSL produced by BtaI2. To test the hypothesis we first screened fluid taken from *B. thailandensis* cultures at various cell densities (FIG. 4). To obtain the fluid, cells were removed by centrifugation and the supernatant fluid was subjected to microfiltration. The filtered culture fluid was used to saturate paper diffusion discs, which were placed on agar plates containing a growing lawn of *Bacillus subtilis*. After overnight incubation at 37° C. a zone of *B. subtilis* growth inhibition was observed around discs, which had been saturated with fluid from stationary phase cultures but not around discs saturated with fluid from logarithmic phase cultures (FIG. 4). Thus *B. thailandensis* produces a secondary metabolite with antimicrobial activity.

We tested the specificity of the antibacterial component from stationary phase culture fluid ($OD_{600}$ 9-10) by using the diffusion disc assay to assess whether the component inhibited growth of other bacterial species. Growth of all of the Gram-positive bacteria tested was inhibited (*S. auerus* including MRSA, *Listeria monocyfogenes*, and *Streptococcus pyogenes*). Neither of the two Gram-negative bacteria we tested, *E. coli* and *Pseudomonas fluorescens*, showed growth inhibition by *B. thailandensis* culture fluid.

E) The btaR2-btaI2 Quorum Sensing System is Required for Antibiotic Production.

To determine whether stationary-phase antibiotic production required the btaR2-btaI2 quorum-sensing system we first asked whether synthesis of the factor required acyl-HSL signaling as follows: We tested cell-free stationary phase culture fluid of a *B. thailandensis* strain with mutations in all three of the acyl-HSL synthase genes, btaI1, I2 and I3 for anti-*B. subtilis* activity as described above (FIG. 5). Fluid from cultures of the triple acyl-HSL synthase mutant, JBT112, did not block *B. subtilis* growth unless the cultures were grown in the presence of added 3OHC8-HSL or 3OHC10-HSL. Addition of C8-HSL was unable to restore antibiotic production to JBT112. As a control we determined that 3OHC10-HSL alone does not have antibiotic activity (FIG. 5). From this experiment we conclude that a BtaI2-produced acyl-HSL is required for production of the antibacterial factor.

To ask whether the acyl-HSL-dependent production of antibacterial activity required BtaR2 we tested the ability of the btaR2 mutant, JBT108, to produce an antibacterial factor. As shown in FIG. 6A, fluid from a stationary phase JET108 culture does not inhibit growth of *B. subtilis* and the antibiotic synthesis phenotype was complemented by a plasmid-borne copy of btaR2. Another way to assess antimicrobial activity is to incubate *B. subtilis* in broth containing fluid from stationary phase *B. thailandensis* cultures and assess bacterial growth as changes in colony-forming units (CFUs) (FIG. 6B). When we incubated *B. subtilis* in medium containing 50% (vol/vol) fluid from a wild-type *B. thailandensis* stationary phase culture, the *B. subtilis* cell density did not change from that of the inoculum. In the presence of 50% (vol/vol) fluid from a stationary phase culture of the btaR2 mutant, JET1 08, the *B. subtilis* cell density increased to that seen in the absence of *B. thailandensis* culture fluid. This difference in CFUs was also observed when we used 10% (vol/vol) *B. thailandensis* culture fluid from either wild type or JBT108 (FIG. 6B). This experiment supports the conclusion that BtaR2-dependent quorum sensing is required for production of the antibacterial factor. It also suggests that the factor exerts bacteriostatic activity rather than bacteriocidal activity.

F) A Biosynthetic Locus (bta Cluster) for Quorum Sensing Regulated Antibiotic Production in *B. Thailandensis* Includes Genes 1233-1241.

As discussed in a previous section the btaI2 gene cluster and a cluster of genes located upstream of btaR2 encode proteins annotated as NRPS and PKS enzymes, which we predict are responsible for the production of the BtaR2—BtaI2 controlled antibiotic. The cluster of genes distal to btaR2 (1233-1241) is predicted to constitute an operon. We first asked whether the promoter upstream of the first gene in the cluster, 1233, was quorum-sensing controlled by constructing a transcriptional fusion of −409 to +I3 (with respect to the predicted translational start site) of the putative 1233 promoter to lacZ. We introduced a 1233-promoter-lacZ fusion plasmid into *E. coli* containing a BtaR2 expression vector and tested whether either 3OHC8-HSL or 3OHC10-HSL activated the lacZ reporter (FIG. 7A). Either 3OHC8-HSL or 3OHC10-HSL was sufficient for BtaR2-dependent induction of lacZ.

To obtain further data about quorum sensing control of the 1233-1241 genes we compared 1233, 1236 and 1239 transcript levels in the wild type and the btaR2 JBT108 mutant by qRT-PCR. The wild type showed about 10-fold more transcript for these genes compared to the mutant (FIG. 7B). Therefore we conclude that BtaR2 and either 3OHC8-HSL or 3OHC10-HSL regulate a cluster of putative secondary metabolite genes including 1233, 1236 and 1239.

To determine whether gene 1233 itself is required for antibiotic production we constructed a 1233 insertion mutant strain and a 1233 in-frame deletion strain of *B. thailandensis* and tested stationary phase culture fluid from both of these 1233 mutants for antibiotic activity. Neither strain made detectable levels of the antibiotic (FIG. 8). Thus, gene 1233 on Chromosome II is required for antibiotic production. We have not tested any of the other genes in the 1233-1241 cluster but we suspect that all or several are required for antibiotic production.

Example 3

Purification and Characterization of Bactobolin, Bactobolin B, Bactobolin C and Bactobolin D A) Isolation, Purification and Characterization of Bactobolin Analogs from Antibiotics Produced by *B. Thailandensis*.

To isolate the antibiotic, *B. thailandensis* was cultivated as disclosed supra. The antibiotic's highly polar, amphoteric nature and its optimal production in rich media (LB) necessitated unusual chromatographic steps. Using activity-guided fractionation against *B. subtilis* 3610, four active compounds were purified, and their structures elucidated by 1-D/2-D NMR (Tables 3-A1-3-A4), HR-MS and MS/MS (Table 3-A5) methods.

General Procedures.

1H and 2-D NMR spectra for bactobolins were recorded in the inversedetection probe of a Varian Inova spectrometer (600 MHz for 1 H, 150 MHz for 13C). 13C NMR spectra were recorded on the same instrument with a broad-band probe. Optical rotations were measured on an Autopol IV Automatic Polarimeter (Rudolph Research Analytical). HPLC purifications were carried out on an Agilent 1100 or 1200 Series HPLC system equipped with a photo diode array detector. LC-MS analysis was carried out on an Agilent 1200 Series HPLC system equipped with a diode array detector and a 6130 Series ESI mass spectrometer using an analytical Thermo Scientific Hypercarb column (5 μm, 4.6×100 mm) operating at 0.7 mL/min with a gradient of 10% MeCN in H2O to 100% MeCN over 25 min. High resolution mass spectrometry (HR-MS) and tandem MS (MS/MS) were performed at the University of Illinois Urbana-Champaign Mass. Spectrometry Facility. Activity assays for activity-guided fractionation were performed using the disc diffusion assay on LB-Agar plates and overnight cultures of *B. subtilis* 3610 or *B. subtilis* 168 in LB as the test organism.

Cultivation of *B. Thailandensis*.

*B. thailandensis E*264 was obtained from DSMZ. All cultivation was carried out on a shaker/incubator at 30° C. and 250 rpm, unless otherwise noted. A small 5 mL culture of *B. thailandensis* in LB was grown to saturation overnight. A 500 mL Erlenmeyer flask containing 125 mL of LB was inoculated with 1 mL of the overnight culture, and subsequently grown to saturation overnight. Each of three 4 L Erlenmeyer flasks containing LB+50 mM Mops, pH 7.0, were inoculated with 15 mL of the overnight culture and grown for three days at 30° C. and 225 rpm. The cells were pelleted by centrifugation (8000 g, 12 min, 4° C.) and bactobolins purified as described below.

Purification of Bactobolins.

1.5 L of the cell-free *B. thailandensis* supernatant from above was loaded directly onto an HP-20 column (~120 mL, d=2.5 cm, I=25 cm), which had been equilibrated in water, at ~5 mL/min. bactobolin eluted in the flow-through, which was loaded directly onto a DEAE column (~80 mL, d=2.5 cm, I=17 cm), which had been equilibrated in water, at ~5 mL/min. bactobolin eluted in the flow-through. These initial columns do not bind bactobolin, but provide a crude separation of bactobolin from non-polar and small negatively charged molecules. The flow-through was concentrated 10-fold in vacuo and stored at 4° C. overnight. A precipitate that forms after these steps was removed by centrifugation and the supernatant, which contains bactobolin, loaded onto a Hypercarb column (Thermo Scientific, ~25 mL, d=1.25 cm, I=20 cm), which had been equilibrated in 20% MeCN in water. The column was washed with 5-7 column volumes (CV) of 20% MeCN, then 10 CV of 50% MeCN in water, and finally with 8-10 CV of 100% MeCN; bactobolin eluted in the 50% MeCN fraction, which was concentrated ~12-fold in vacuo and then loaded with successive 2 mL injections onto an Agilent Eclipse C8 column (5 μm, 9.4×250 mm). bactobolin eluted at 25-30% MeCN in H2O. Fractions containing bactobolin were pooled, concentrated and separated to individual congeners on a Supelco Discovery HS C18 column (10 μm, 10×250 mm) with an isocratic gradient of 12% MeCN (+0.1% formic acid) in H2O (+0.1% formic acid) over 25 minutes, followed by a gradient from 12 to 45% of MeCN (+0.1% formic acid) over 15 minutes. This was repeated to obtain each analog in >95% purity (as judged by NMR). bactobolins A, B, C, and D eluted at 11, 14, 20, and 29 minutes with a yield of 9, 8, 14 and 1.5 mg per 1.5 L, respectively.

Characterization of Bactobolin Analogs Using NMR Spectra.

NMR data for bactobolin A are summarized in Tables 3-A1:

TABLE 3-A1

Bactobolin A

NMR spectral data for bactobolin A.

| C/H | $\delta_H$ | Multiplicity (Hz) | $\delta_C$ | HMBC |
|---|---|---|---|---|
| 1 | | | 169.4 | |
| 3 | | | 86.2 | |
| 3a | 6.18 | s | 74.4 | C3, C3b, C4 |
| 3b | 1.74 | s | 18.4 | C3, C3a, C4 |
| 4 | 4.94 | d (3.4) | 46.6 | C3, C5, C9, C10 |
| 5 | 3.16 | t (9.5) | 70.9 | C4, C6, C10 |
| 6 | 3.97 | dt (6.8, 9.8) | 68.7 | C5, C7, C10 |
| 7 ($H_e$) | 2.95 | dd (6.7, 18.8) | 36.4 | C5, C6, C8, C9 |
| 7 ($H_a$) | 2.46 | ddd (2.4, 10.0, 18.9) | 36.4 | C6, C8, C9 |
| 8 | | | 175.8 | |

TABLE 3-A1-continued

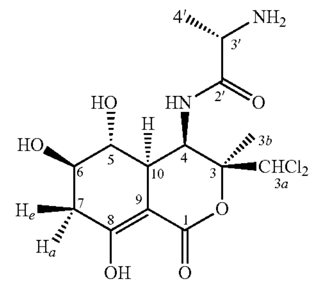

Bactobolin A

NMR spectral data for bactobolin A.

| C/H | $\delta_H$ | Multiplicity (Hz) | $\delta_C$ | HMBC |
|---|---|---|---|---|
| 9 | | | 89.5 | |
| 10 | 3.10 | m | 38.4 | C5, C9 |
| 2' | | | 171 | |
| 3' | 4.17 | q (7.1) | 49.2 | C2', C4' |
| 4' | 1.55 | d (7.1) | 17.3 | C2', C3' |

NMR data for bactobolin B are summarized in Tables 3-A2:

TABLE 3-A2

Bactobolin B

NMR spectral data for bactobolin B.

| C/H | $\delta_H$ | Multiplicity (Hz) | $\delta_C$ | HMBC |
|---|---|---|---|---|
| 1 | | | 169.7 | |
| 3 | | | 86.2 | |
| 3a | 6.19 | s | 74.5 | C3, C3b, C4 |
| 3b | 1.72 | s | 18.2 | C3, C3a, C4 |
| 4 | 4.88 | d (3.3) | 46.5 | C9, C10, C2' |
| 5 | 3.20 | t (9.5) | 70.8 | C4, C6, C7, C10 |
| 6 | 3.96 | dt (6.9, 9.8) | 68.7 | C5, C7 |
| 7 ($H_e$) | 2.94 | dd (6.7, 18.8) | 36.3 | C5, C6, C8, C9 |
| 7 ($H_a$) | 2.46 | ddd (2.2, 10.0, 18.9) | 36.3 | C6, C8, C9 |
| 8 | | | 175.7 | |
| 9 | | | 89.5 | |
| 10 | 3.06 | m | 38.3 | C5, C8, C9 |
| 2' | | | 174.8 | |
| 3' | 4.41 | q (7.1) | 49.9 | C2', C4', C6' |
| 4' | 1.41 | d (7.2) | 16.7 | C2', C3' |
| 6' | | | 170.6 | |
| 7' | 4.09 | q (7.1) | 48.9 | C6', C8' |
| 8' | 1.53 | d (7.1) | 16.7 | C6', C7' |

NMR data for bactobolin C are summarized in Tables 3-A3:

TABLE 3-A3

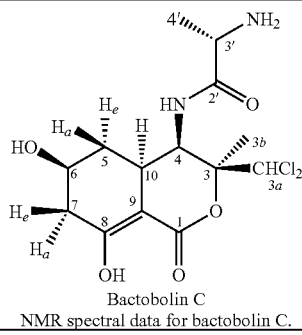

Bactobolin C
NMR spectral data for bactobolin C.

| C/H | $\delta_H$ | Multiplicity (Hz) | $\delta_C$ | HMBC |
|---|---|---|---|---|
| 3 | | | 85.3 | |
| 3a | 6.15 | s | 74.3 | C3, C3b |
| 3b | 1.74 | s | 18.2 | C3, C3a, C4 |
| 4 | 4.72 | d (3.6) | 49.1 | C9, C10 |
| 5 ($H_a$) | 2.08 | m | 33.5 | C4, C6, C10 |
| 5 ($H_e$) | 1.15 | q (11.6) | 33.5 | C4, C6, C7, C10 |
| 6 | 4.17 | m | 64.4 | |
| 7 ($H_e$) | 2.85 | dd (6.4, 18.6) | 37.5 | C5, C6, C8, C9 |
| 7 ($H_a$) | 2.35 | ddd (2.5, 9.9, 18.6) | 37.5 | C6, C8, C9 |
| 8 | | | 176.7 | |
| 9 | | | 91.4 | |
| 10 | 3.30 | m | 31.8 | |
| 2' | | | 171.1 | |
| 3' | 4.16 | m | 49.1 | C2', C4' |
| 4' | 1.55 | d (7.1) | 17.2 | C2'. C3' |

NMR data for bactobolin D are summarized in Tables 3-A4:

Table 3-A4

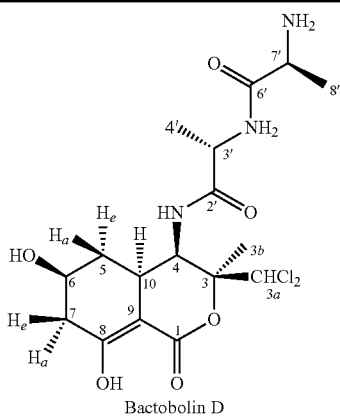

Bactobolin D
NMR spectral data for bactobolin D.

| C/H | $\delta_H$ | Multiplicity (Hz) | $\delta_C$ | HMBC |
|---|---|---|---|---|
| 3 | | | 85.8 | |
| 3a | 6.17 | s | 74.5 | C3, C3b |
| 3b | 1.73 | s | 18.1 | C3, C3a, C4 |
| 4 | 4.66 | d (3.6) | 49.1 | C9, C10 |
| 5 ($H_a$) | 2.05 | m | 33.7 | C6 |
| 5 ($H_e$) | 1.18 | m | 33.7 | C4, C10 |
| 6 | 4.16 | m | 64.2 | |
| 7 ($H_e$) | 2.85 | dd (6.3, 18.6) | 37.6 | C5, C6, C8, C9 |
| 7 ($H_a$) | 2.35 | ddd (2.4, 9.9, 18.5) | 37.6 | C6, C8, C9 |
| 8 | | | 176.2 | |
| 9 | | | 91.4 | |
| 10 | 3.28 | m | 31.8 | |

Table 3-A4-continued

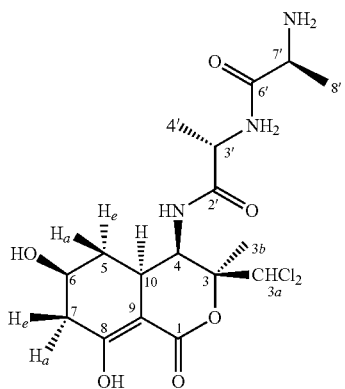

Bactobolin D
NMR spectral data for bactobolin D.

| C/H | $\delta_H$ | Multiplicity (Hz) | $\delta_C$ | HMBC |
|---|---|---|---|---|
| 2' | | | 174.8 | |
| 3' | 4.41 | q (7.2) | 49.9 | C2', C4', C6' |
| 4' | 1.41 | d (7.2) | 16.7 | C2', C3' |
| 6' | | | 170.2 | |
| 7' | 4.09 | q (7.1) | 48.9 | C6', C8' |
| 8' | 1.52 | d (7.1) | 16.6 | C6', C7' |

The stereochemistry of bactobolin A can be demonstrated using the data summarized supra. The large coupling between H5 and H6 (9.5-9.8 Hz) suggests an axial-axial relationship between these protons. H10 couples to H5 with a similar coupling constant resulting in a triplet H5 signal and indicating an axial-axial interaction between H5-10. H4 appears as a doublet with a 3.3 Hz coupling to H10 indicating an equatorial-axial interaction between H4-H10. H10 is also involved in homoallylic coupling interaction with H7ax with a constant of 2.4 Hz consistent with the axial position of H10. This orientation is consistent with the ROESY interactions (FIG. 9). The ROESY signal between H4 and H3b indicates an S orientation at C3 (the interaction highlighted with arrow 1 in FIG. 9). There is also a ROESY correlation between H3b and H10 consistent with an axial H10 and an S configuration at C3 (The interaction highlighted with arrow 2 in FIG. 9). H5 shows a weak ROESY signals to H4' indicated with arrow 3 in FIG. 9. A similar analysis has been applied to other bactobolins with a similar outcome (see Tables 3-A1-3-A4).

The stereochemistry is based on $[\alpha]_D$ comparisons (Table 3-A5):

TABLE 3-A5

Spectral properties of bactobolins.

| | Bactobolin A | Bactobolin B | Bactobolin C | Bactobolin D |
|---|---|---|---|---|
| HR – MS (M + H)obs[a] | 383.0777 | 454.1148 | 367.0828 | 438.1212 |
| HR – MS (M + H)calc | 383.0769 | 454.1145 | 367.0823 | 438.1199 |
| MS/MS (M + H)obs[b] | 312.1 | 312.1 | 296.1 | 296.1 |
| MS/MS (M + H)calc[b] | 312.2 | 312.2 | 296.2 | 296.2 |
| $[\alpha]_D$ (c = 1, $H_2O$)[c] | −6.3° | −26.7° | −17.8° | −12.9° |

TABLE 3-A5-continued

Spectral properties of bactobolins.

| | Bactobolin A | Bactobolin B | Bactobolin C | Bactobolin D |
|---|---|---|---|---|
| $[\alpha]_{D(reported)}{}^d$ | −6.3° | −27° | −23.9° | nr[e] |
| $\lambda_{max}$ (nm) | 264 | 264 | 266 | 266 |

[a]HR – MS and MS/MS data were acquired under positive ionization mode.
[b]MS/MS spectra were acquired under positive ionization mode. The observed (M + H) of the dominant peak is indicated, and corresponds to bactobolin minus the Ala or Ala-Ala fragment.
[c]The specific rotation data have been scaled to c = 1 for comparison with published values. Optical rotation for bactobolins A, B, C, and D were obtained with c = 0.9, c = 0.8, c = 1 and c = 0.15, respectively.
[d]The reported $[\alpha]_D$ data are from reference 1.
[e]nr, not reported.

J coupling and ROESY spectral analyses which confirm the axial-axial relationship of protons $H_5/H_{10}$ and $H_5/H_6$, the axial-equatorial relationship of $H_{10}/H_4$, and the homoallylic coupling between $H_{10}$ and $H_{7ax}$.[1,26] The stereochemistry of the Ala residue(s) was confirmed by acid hydrolysis followed by the following experiment:[27]

To determine the absolute configuration of the Ala residues in bactobolin, 0.1-0.7 mg of bactobolin A-D was dissolved in ~1 mL of 6 N HCl in a 4 mL scintillation vial and heated in an oil bath at 115° C. for 1.5 h. The acid was removed in vacuo and the material re-dissolved ~1 mL in water. This was repeated 2× to completely remove the acid. Each sample was then loaded onto a PrepSep C8 cartridge (Fisher Scientific) and Ala was eluted with 10% MeCN in H2O. The eluant was dried in vacuo and Marfey's analysis was carried out as previously described. Bactobolins B-D only contained L-Ala, bactobolin A contained ~18% D-Ala which presumably arose from racemization during extended storage of bactobolin A under acidic conditions (0.2%) TFA).

B) Export of Bactobolin.

The btaK mutant and btaI1, I2, I3 mutants have been described (see Table 3-B). The btaT deletion mutant was generated by a method previously described. Overlap extension PCR was used to generate PCR products with ~1 kb of DNA homologous to the DNA flanking the btaT gene. The products were annealed and amplified by PCR. This step introduced primer-encoded XbaI and HindIII sites during amplification. The digested PCR products were ligated to XbaI-HindIII-digested pJRC115 and this suicide vector was introduced into *B. thailandensis* E264 to deliver the btaT deletion allele. Correct clones were identified by PCR amplification of the ΔbtaT allele. These were further confirmed by sequencing PCR products generated with primers targeting chromosomal DNA flanking the recombination sites.

TABLE 3-B

| Bacterial strains used in this study. | |
|---|---|
| Strain | Source |
| *Burkholderia thailandensis* E264 wt | DSMZ,[28] |
| *Burkholderia thailandensis* ΔbtaK (BD20) | Ref.[29], |
| *Burkholderia thailandensis* ΔbtaT (BD44) | This study |
| *Burkholderia thailandensis* ΔbtaI1, I2, I3 (JBT112) | Ref.[30] |
| *Staphylococcus aureus* COL (methicillin resistant MRSA strain) | Ref.[31] |
| *Enterococcus faecalis* V583 (vancomycin resistant VRE strain) | Ref.[32] |
| *Vibrio parahaemolyticus* LM5674 | Ref.[33] |
| *Bacillus subtilis* 3610 | Ref. 11[34] |
| *Escherichia coli* ATCC25922 | ATCC |

C) Antibiotic Assays of Bactobolin Analogs.

To test the potency of bactobolins, antibiotic assays were carried out against the human pathogens MRSA, VRE and *V. parahaemo-lyticus*, and against *B. subtilis* and *E. coli* (Table 3-C).

The minimum inhibitory concentrations (MIC) of each bactobolin was determined according to the 2003 guidelines of the Clinical and Laboratory Standards Institute (CLSI, formerly NCCLS) using the microtiter MIC method. Inocula for each test organism were prepared by suspending a colony from an LB agar plate into Tryptic Soy Broth and growing for 3-5 hours at 35° C. with shaking, then adjusting the culture turbidity in PBS to the equivalent of a 1.0 McFarland Standard (3×108 CFU/ml). These cell suspensions were used as inocula for microtiter MIC assays. 2.5 μL inoculum, which corresponded to 1×106 cells, was added to a 200 μL well containing each bactobolin diluted in cation-adjusted Mueller-Hinton II broth (actual CFU/ml ranged from 5×104 to 1×106), and these were incubated without shaking for 24 hours at 35° C. The MIC was defined as the lowest concentration of bactobolin (μg/ml) in which bacterial growth in the well was not measurable by determining the turbidity at 595 nm (A595) on a 96-well plate reader. See Table S8 for strains used in these assays.

TABLE 3-C

| Minimum Inhibitory Concentration (MIC, μg/mL)[a] of bactobolins A, B, C, or D against selected bacterial strains. | | | | |
|---|---|---|---|---|
| Strain | A | B[b] | C[c] | D |
| *S. aureus* COL (MRSA) | 0.78 | 0.29 | 6.25 | 37.5 |
| *E. faecalis* V583 (VRE) | >25 | 25 | >25 | nd[b] |
| *V. parahaemolyticus* LM5674 | 0.20 | 0.20 | 1.56 | nd[b] |
| *B. subtilis* 3610 | 1.56 | 0.39 | 12.5 | 100 |
| *E. coli* ATCC25922 | 6.25 | 1.56 | 25 | >100 |

[a]The MIC was determined according to the CLSI assay (see SI). The values are the average from two independent experiments.
[b]nd, not determined.

The results show that bactobolins A and B, which contain the hydroxyl group at C5 are more potent than bactobolins C and D. Bactobolin D is the weakest analog consistent with its role as a biosynthetic precursor and its low isolation yield. Bactobolins A and B are potent antibiotics against MRSA and *V. parahaemolyticus* with MICs <1 μg/mL. Bactobolin C is also is also effective against these strains, though to a lesser extent. All three analogs displayed low activity against VRE.

Example 4

Annotation of the bta Cluster

Bactobolins have several interesting structural features. As suggested by the bta cluster, they are NRPS-PKS hybrids containing a di or tripeptide fused to a C6-polyketide. The fusion occurs at the carboxyl group of 2-hydroxy-3,3-dichlorovaline (OH—$Cl_2$-Val), an unnatural amino acid with unknown biosynthesis that is thus far limited to the bactobolins. The enol lactone likely mimics a carboxyl group allowing bactobolins to enter the cell via di- and tripeptide transporters.[35] Bactobolins differ from actinobolin, an antibiotic identified from *Streptomyces griseoviridis*, in that the OH—$Cl_2$-Val residue is replaced by Thr.[26a] This switch renders actinobolin 21-fold, 1000-fold and 900-fold less active than bactobolin in *E. coli* kill-assays, in vitro inhibition of translation, and murine antitumor activity, respectively.[36] Bta-based bioinformatic searches for its relatives show that bta is confined to the *Burkholderia* genus (FIG. S7). This suggests that the biosynthesis of OH—$Cl_2$-Val and its incorporation into the actinobolin framework evolved only in the *Burkholderia* lineage.

The identification of bactobolin and its link to the bta cluster allows us to propose a scheme for its biosynthesis. The modular 44 kb PKS/NRPS cluster is highly fragmented with product(s) inconsistent with the co-linearity rule (Scheme 1A). Based on short intergenic sequences and a single Shine-Dalgarno sequence, the translation of btaK-btaS appears to occur from one polycistronic mRNA. The cluster contains six distinct elements: genes involved in regulation (I2 and R2), metabolite/product transporters (F, G, T, and V), synthesis of OH—Cl2-Val (B, C, D, E, and H), Ala-Ala (K and N) and the C6 polyketide (L, M, O, P, and S), and tailoring reactions (A, Q and U) (Scheme 1A). Results of homology searches and other bioinformatic analyses (e.g. FASTA search results for proteins in the bta cluster summarized in Table 4-1) lead us to propose the model in Scheme 1B.

TABLE 4-1

FASTA search results for proteins in the bta cluster.

| Gene | No. of amino acids | Protein homology (Swissport accession no.) | % Amino acid identity[a] |
|---|---|---|---|
| btaA | 381 | *Burkholderia multivorans* CGD1, 4-hydroxyphenyl-pyruvate dioxygenase (B9B0B6) | 79.5 |
| btaB | 98 | No significant homology[b] | |
| btaC | 307 | *Burkholderia pseudomallei* MSHR346, CmaB chlorinase (C4I3I8) | 97.1 |
| btaD | 81 | *Burkholderia pseudomallei*, putative acyl-carrier protein (Q63L26) | 91.1 |
| btaE | 548 | *Burkholderia pseudomallei* 1106b, Linear gramicidin synthetase subunit C - adenylation domain (C5ZLJ3)[c] | 89.0 |
| btaF | 135 | No significant homology | |
| btaG | 410 | *Burkholderia pseudomallei*, CPA2 family transporter (C0YG66) | 93.4 |
| btaH | 285 | No significant homology[d] | |
| btaI2 | 206 | *Burkholderia pseudomallei* S13, autoinducer synthetase (B1H6I9) | 91.7 |
| btaJ | 693 | *Burkholderia pseudomallei* 406e, oligopeptidase A (A8ELY3) | 86.9 |
| btak | 1446 | *Burtholderia pseudomallei*, putative non-ribosomal peptide synthase (Q63L34)[e] | 82.4 |

TABLE 4-1-continued

FASTA search results for proteins in the bta cluster.

| Gene | No. of amino acids | Protein homology (Swissport accession no.) | % Amino acid identity[a] |
|---|---|---|---|
| btaL | 1524 | *Burkholderia pseudomallei*, type I polyketide synthase (A3NJX3)[f] | 86.4 |
| btaM | 1370 | *Burkholderia pseudomallei*, TubD-like polyketide synthase (Q3JMA6)[g] | 91.4 |
| btaN | 1144 | *Burkholeria pseudomallei*, putative non-ribosomal pepdite synthase (A4MH51)[h] | 88.1 |
| btaO | 779 | *Burkholderia pseudomallei* Pakistan 9, type I polyketide synthase (C0YG77)[i] | 84.2 |
| btaP | 530 | *Burkholderia pseudomallei* 668 Metallo-β-lactamase family protein (A3NJW9) | 94.5 |
| btaQ | 281 | *Burkholderia pseudomallei* Pakistan 9, GNAT family acetyltransferase (C0YG79) | 90.4 |
| btaR2 | 234 | *Burkholderia pseudomallei*, N-acyl homoserine lactone-dependent regulatory protein (Q3JMA2) | 95.3 |
| btaS | 280 | *Burkholderia pseudomallei* 1106a, type II thioesterase (A3P5I5) | 92.8 |
| btaT | 408 | *Burkholderia pseudomallei* 1106 a, Major facilitator superfamily/drug resistance protein (C5ZLH5) | 90.7 |
| btaU | 281 | *Burkholderia pseudomallei* MSHR346 TauD/TfdA (C4I3G5) | 94.7 |

[a]Results are from FASTA searches conducted between Jul. 5, 2009 and Sep. 1, 2009.
[b]InterProScan searches indicate similarities to an ACP-like domain.

[c]The NRPS Predictor software indicates valine specificity for this domain.

[d]InterProScan searches indicate similarities to members of the α/β hydrolase superfamily.

[e]InterProScan searches indicate a domain architecture of C-A-TC, corroborated by analysis of the individual domains, where the initial C domain appears to be inactive. NRPS prediction software indicates Gly specificity for the A domain.

[f]InterProScan searches suggest a domain architecture of KS-AT-SDR-ACP. No homology was found for a ~300 amino acid stretch preceding the SDR domain.

[g]InterProScan searches suggest a domain architecture of KS-KR-ACP, the presence of the AT domain is inferred from results of secondary structure prediction searches using Phyre software.

[h]InterProScan and NRPS prediction software searches indicate an A-T-C-T domain architecture and Ala specificity for the A domain.

[i]InterProScan searches indicate a KS-AT-ACP architecture.

Scheme 1.

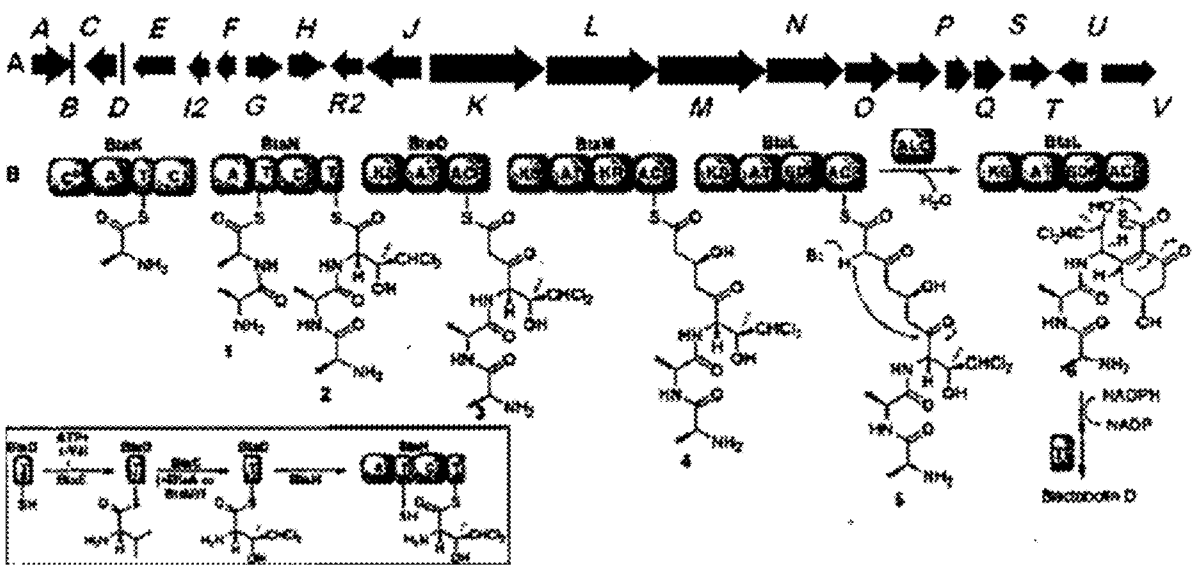

(A) Schematic of the bactobolin gene cluster. (B) Proposed biosynthetic scheme for bactobolin D. Note that the aldol condensation (ACL) and thioesterase (TE) reactions are not assigned to a specific protein or domain. See text for details. Inset, proposed biosynthesis of $OH \cdot Cl_2Val$.

Biosynthesis of OH—Cl$_2$-Val entails both dichlorination and hydroxylation reactions. Dichlorination likely involves BtaC, a Fe chlorinase (57% identical to CytC3). BtaC contains an Ala residue, typical for Fe chlorinases, in place of the carboxylate group that usually occupies the facial triad and coordinates Fe in α-KG-dependent oxygenases.[37] Hydroxylation of Val (or Cl$_2$-Val) could be catalyzed by either BtaA or BtaU, both non-heme Fe-dependent dioxygenases, or even by BtaC as recent studies have delineated the requirements for Cl vs OH insertion by these enzymes.[38] BtaC is flanked by two free-standing thiolation (T) domains, where BtaB lacks the typical GXDS(L/I) sequence motif and may be inactive.[39] Thus, BtaD is likely the active T domain and may be primed with Val by BtaE, a Val-specific, stand-alone adenylation (A) domain. BtaH contains a GXCX(G/S) motif and likely acts as an CmaE-like transacylase,[40] by shuttling the assembled OH—Cl2-Val from one T domain to another within the NRPS assembly line (Scheme 1, inset).

BtaK and BtaN are NRPSs with the domain architecture shown in Scheme 1B. The first condensation (C) domain in BtaK does not contain the conserved active site motif (HHX3DG) and is likely inactive.[39] Its A domain bears higher homology to Gly-specific domains, but no Gly-bearing bactobolins have been detected experimentally. In contrast the A domain of BtaN has an Ala-specific sequence. After formation of Ala-Ala (1), the C-terminal T domain of BtaN likely accepts the activated OH—Cl2-Val, which the adjacent C domain may assemble into an Ala-Ala-(OH—Cl$_2$-Val) tripeptide (2). This is subsequently condensed to an acetyl group originating from malonyl CoA catalyzed by the ketosynthase (KS) domain of BtaO (3), followed by another acetyl group addition and ketoreduction (KR) by BtaM to give 4. The final C2 unit may be added by BtaL yielding 5. BtaL contains a non-canonical KR domain that is similar to short chain dehydrogenases (SDR). There is a 300 amino acid region between the AT and SDR domains with no recognizable sequence homology. The ensuing plausible reactions that may yield bactobolin, aldol condensation between OH—Cl2-Val and the final malonyl-CoA unit and elimination of water to give 6, followed by reduction of the resulting α,β-unsaturated ketone generating the enol moiety (Scheme 1A) lack clear precedents at this time. These reactions may be performed by the SDR domain in BtaL and the adjoining 300 amino acid region (Secondary structure predictions show that this 300 amino acid region is SDR-like. Recent studies have suggested that a KR domain (SDR-like) involved in erythromycin biosynthesis stabilizes an enolate intermediate, which is required for enzymatic aldol reactions proposed herein.);[41] in this case, BtaS would act as a thioesterase to generate the lactone. Alternatively, they could be carried out by BtaS, BtaP (a "-lactamase), and the SDR domain in BtaL in accordance with studies by Fujii et al. who have shown a Claisen-like condensation catalyzed by a thioesterase,[42] and recent reports implicating a "-lactamase in a thioesterase reaction (Table 4-1).[43] Mutational analyses and biochemical studies are in progress to distinguish between these options.

Finally, the cluster appears to provide an indication of how four analogs are biosynthesized by one cluster.[44] The hydroxyl group at C5 may be inserted by BtaA or BtaU. BtaQ and BtaJ bear high homology to an acetyltransferase and an oligopeptidase, respectively. Indeed acetylated bactobolins have previously been reported[1] N-acetyl peptides are good substrates for oligo-peptidases,[45] which could cleave Nacetyl-bactobolin B or D, generated by BtaQ, to yield bactobolin A or C, respectively. Thus, a promiscuous hydroxylase and an oligopeptidase may generate three additional congeners from bactobolin D.

To begin to test the predictions above, mutational and biochemical analyses have been carried out to examine the export of bactobolin as a means of host resistance. We investigated a markerless quorum sensing defective mutant, which does not express btaK-btaS and thus does not produce bactobolin.[30, 29] Addition of exogenous bactobolin showed that the mutant was resistant indicating that the resistance genes lie outside of this region and that their expression is not quorum-controlled (Tables 4-2 & 4-3) (Exogenous bactobolin was added in the form of filtered culture supernatants of wt B. thailandensis E264, which contained 40±18 µg/mL bactobolin as quantitated by LC-MS using purified standards.).

TABLE 4-2

Susceptibility of wt B. thailandensis, ΔbtaI1/I2/I3 or ΔbtaT to bactobolin B or spent medium from wt B. thailandensis.

| Strain | Bactobolin B MIC (µg/ml)$^a$ | Susceptible to spent medium of wt B. thailandensis? |
| --- | --- | --- |
| B. thailandensis E264 (wt) | >25 | No |
| B. thailandensis ΔbtaI1, I2, I3 (JBT112) | >25 | No |
| B. thailandensis ΔbtaT (BD44) | >25 | No |

$^a$Susceptibility of B. thailandensis strains was determined using the CLSI microtiter MIC assay (described above) using purified bactobolin B or filter sterilized wild type culture fluid prepared from wt B. thailandensis E264 cultures grown shaking in LB + Mops, pH 7 at 30° C. for 24 hours.

BtaT is predicted to be a drug resistance transporter and may be involved in the export of bactobolin. To examine its function, a markerless btaT mutation was generated. Cultivation of this mutant under the same conditions as above for 12 or 24 h showed that export of bactobolin was reduced 18-fold or 10-fold, respectively, relative to wt supporting the role proposed for BtaT. The btaT mutant was also resistant to bactobolin indicating multiple pathways for bactobolin excretion. Consistent with previous analysis, the btaK mutation abrogated bactobolin production (FIG. 10).

Example 5

Preparation of a Composition Comprising a Bactobolin Analog Using a Bacterial Culture Comprising a Bacterial Cell Inserted with the Bta Cluster Example 6

Preparation, Isolation and Purification of a Bactobolin Analog from the Composition Prepared in Example 5

Example 7

Preparation of a Composition Comprising a Bactobolin Analog Using a Bacterial Culture Comprising a Bacterial Cell Comprising a Mutant Bta Cluster Example 8

Preparation, Isolation and Purification of a Bactobolin Analog from the Composition Prepared in Example 7

REFERENCES

The following references are incorporated herein by reference in their entirety:

1) T. Munakata, H.-I. Sakai, H. Matsuki, K. Isagai, *Yakugaku Zasshi* 1981, 101, 132.
2) Zhang, Z., S. Schwartz, L. Wagner, and W. Miller. 2000. A greedy algorithm for aligning DNA sequences. J. Comput. Biol. 7203-14.
3) Newman, J. R., and C. Fuqua. 1999. Broad-host-range expression vectors that carry the L-arabinose-inducible *Escherichia coli* araBAD promoter and the araC regulator. Gene 227: 197-203.
4) Farinha, M. A., and A. M. Kropinski. 1990. Construction of broad-host-range plasmid vectors for easy visible selection and analysis of promoters. J. Bacteriol. 172:3496-99.
5) Wuthiekanun, V., M. D. Smith, D. A. Dance, A. L. Walsh, T. L. Pitt, and N. J. White. 1996. Biochemical characteristics of clinical and environmental isolates of *Burkholderia pseudomallei*. J. Med. Microbiol. 45:408-12.
6) Cardona, S. T., and M. A. Valvano. 2005. An expression vector containing a rhamnoseinducible promoter provides tightly regulated gene expression in *Burkholderia cenocepacia*. Plasmid 54:219-28.
7) Barrett, A. R., Y. Kang, K. S. Inamasu, M. S. Son, J. M. Vukovich, and T. T. Hoang. 2008. Genetic tools for allelic replacement in *Burkholderia* species. Appl. Environ. Microbiol. 74:4498-508.
8) Gould, T. A., J. Herman, J. Krank, R. C. Murphy, and M. E. Churchill. 2006. Specificity of acyl-homoserine lactone synthases examined by mass spectrometry. J. Bacteriol. 188:773-83.
9) Duerkop, B. A., R. L. Ulrich, and E. P. Greenberg. 2007. Octanoyl-homoserine lactone is the cognate signal for *Burkbolderia mallei* BmaRI-BmaI1 quorum sensing. J. Bacteriol. 189:5034-40.
10) Ralling, G., S. Bodrug, and T. Linn. 1985. Growth rate-dependent regulation of RNA polymerase synthesis in *Escherichia coli*. Mol. Gen. Genet. 201:379-86.
11) Jorgensen, J. H., J. D. Turnidge, and J. A. Washington. 1999. 7th ed. Antibacterial susceptibility tests: Dilution and disc diffusion methods. Manual of clinical microbiology 7th ed. ASM Press. 1526-1543, Washington, D.C.
12) Burkholder, P. R., and N. H. Giles. 1947. Induced biochemical mutations in *Bacillus subtilis*. Amer. J. Bot. 34.
13) Dean, D. H., J. C. Orrego, K. W. Hutchison, and H. O. Halvorson. 1976. New temperate bacteriophage for *Bacillus subtilis*, rho 11. J. Virol. 20:509-19.
14) Schaefer, A. L., B. L. Hanzelka, M. R. Parsek, and E. P. Greenberg. 2000. Detection, purification, and structural elucidation of the acylhomoserine lactone inducer of *Vibrio fischeri* luminescence and other related molecules. Methods Enzymol. 305:288-301.
15) Shaw, P. D., G. Ping, S. L. Daly, C. Cha, J. E. Cronan, Jr., K. L. Rinehart, and S. K. Farrand. 1997. Detecting and characterizing N-acyl-homoserine lactone signal molecules by thin-layer chromatography. Proc. Natl. Acad. Sci. USA 94:6036-41.
16) Song, Y., C. Xie, Y. M. Ong, Y. H. Gan, and K. L. Chua. 2005. The BpsIR quorum-sensing system of *Burkholderia pseudomallei*. J. Bacteriol. 187: 785-90.
17) Duerkop, B. A., J. P. Herman, R. L. Ulrich, M. E. Churchill, and E. P. Greenberg. 2008. The *Burkholderia mallei* BmaR3-BmaI3 quorum-sensing system produces and responds to N-3-hydroxy-octanoyl homoserine lactone. J. Bacteriol. 190:5137-41.
18) Keating, T. A., and C. T. Walsh. 1999. Initiation, elongation, and termination strategies in polyketide and polypeptide antibiotic biosynthesis. Curr. Opin. Chem. Biol. 3:598-606.
19) Ullrich, M., and C. L. Bender. 1994. The biosynthetic gene cluster for coronamic acid, an ethylcyclopropyl amino acid, contains genes homologous to amino acid-activating enzymes and thioesterases. J. Bacteriol. 176: 7574-86.
20) Vaillancourt, F. H., E. Yeh, D. A. Vosburg, S. E. O'Connor, and C. T. Walsh. 2005. Cryptic chlorination by a non-haem iron enzyme during cyclopropyl amino acid biosynthesis. Nature 436: 1191-4.
21) Felnagle, E. A., E. E. Jackson, Y. A. Chan, A. M. Podevels, A. D. Berti, M. D. McMahon, and M. G. Thomas. 2008. Nonribosomal peptide synthetases involved in the production of medically relevant natural products. Mol. Pharm. 5:191-211.
22) Fischbach, M. A., and C. T. Walsh. 2006. Assembly-line enzymology for polyketide and nonribosomal peptide antibiotics: logic, machinery, and mechanisms. Chem Rev 106:3468-96.
23) Lewinson, O., J. Adler, N. Sigal, and E. Sibi. 2006. Promiscuity in multidrug recognition and transport: the bacterial MFS Mdr transporters. Mol Microbiol 61:277-84.
24) Llano-Sotelo, B., E. F. Azucena, Jr., L. P. Kotra, S. Mobashery, and C. S. Chow. 2002. Aminoglycosides modified by resistance enzymes display diminished binding to the bacterial ribosomal aminoacyl-tRNA site. Chem. Biol. 9:455-63.
25) Vetting, M. W., S. d. C. LP, M. Yu, S. S. Hegde, S. Magnet, S. L. Roderick, and J. S. Blanchard. 2005. Structure and functions of the GNAT superfamily of acetyltransferases. Arch. Biochem. Biophys. 433:212-26.
26) a) F. J. Antosz, D. B. Nelson, D. L. Herald, Jr., M. E. Munk, J. Am. Chem. Soc. 1970, 92, 4933; b) S. Kondo, Y. Horiuchi, M. Hamada, T. Takeuchi, H. Umezawa, *J. Antibiotics* 1979, 32, 1071.
27) K. Fujii, Y. Ikai, H. Oka, M. Suzuki, K. Harada, *Anal. Chem.* 1997, 69, 5146.
28) Brett, P. J.; Deshazer, D.; Woods, D. E. *Epidemiol. Infect.* 1997, 118, 137.
29) B. A. Duerkop, J. Varga, J. R. Chandler, S. B. Peterson, J. P. Herman, M. E. Churchill, M. R. Parsek, W. C. Nierman, E. P. Greenberg, *J. Bacteriol.* 2009, 191, 3909.
30) J. R. Chandler, B. A. Duerkop, A. Hinz, T. E. West, J. P. Herman, M. E. Churchill, S. J. Skerrett, E. P, Greenberg, *J. Bacteriol.* 2009, 191, 5901.
31) Gill, S. R.; Fouts, D. E.; Archer, G. L.; Mongodin, E. F.; Deboy, R. T.; Ravel, J.; Paulsen, I. T.; Kolonay, J. F.; Brinkac, L.; Beanan, M.; Dodson, R. J.; Daugherty, S. C.; Madupu, R.; Angiuoli, S. V.; Durkin, A. S.; Haft, D. H.; Vamathevan, J.; Khouri, H.; Utterback, T.; Lee, C.; Dimitrov, G.; Jiang, L.; Qin, H.; Weidman, J.; Tran, K.; Kang, K.; Hance, I. R.; Nelson, K. E.; Fraser, C. M. *J. Bacteriol.* 2005, 187, 2426.
32) Paulsen, I. T.; Banerjei, L.; Myers, G. S.; Nelson, K. E.; Seshadri, R.; Read, T. D.; Fouts, D. E.; Eisen, J. A.; Gill, S. R.; Heidelberg, J. F.; Tettelin, H.; Dodson, R. J.; Umayam, L.; Brinkac, L.; Beanan, M.; Daugherty, S.; DeBoy, R. T.; Durkin, S.; Kolonay, J.; Madupu, R.; Nelson, W.; Vamathevan, J.; Tran, B.; Upton, J.; Hansen, T.; Shetty, J.; Khouri, H.; Utterback, T.; Radune, D.; Ketchum, K. A.; Dougherty, B. A.; Fraser, C. M. *Science* 2003, 299, 2071.
33) Enos-Berlage, J. L.; McCarter, L. L. *J. Bacteriol.* 2000, 182, 5513.
34) Dean, D. H.; Orrego, J. C.; Hutchison, K. W.; Halvorson, H. O. *J. Virol.* 1976, 20, 509.
35) H. Daniel, B. Spanier, G. Kottra, D. Weitz, *Physiology* 2006, 21, 93.

36) M. Hori, K. Suzukake, C. Ishikawa, *J. Antibiotics* 1981, 34, 465.
37) a) L. C. Blasiak, F. H. Vaillancourt, C. T. Walsh, C. L. Drennan, *Nature* 2006, 440, 368; b) D. P. Galonic, E. W. Barr, C. T. Walsh, J. M. Bollinger, Jr., C. Krebs, *Nat. Chem. Biol.* 2007, 3, 113; c) C. Krebs, D. Galonic Fujimori, C. T. Walsh, J. M. Bollinger, Jr., *Acc. Chem. Res.* 2007, 40, 484.
38) M. L. Neidig, et al., *J. Am. Chem. Soc.* 2007, 129, 14224.
39) L. Tang, Y. J. Yoon, C.-Y. Choi, C. R. Hutchinson, *Gene* 1998, 216, 255.
40) E. R. Strieter, F. H. Vaillancourt, C. T. Walsh, *Biochemistry* 2007, 46, 7549.
41) A. T. Keatinge-Clay, R. M. Stroud, *Structure* 2006, 14, 737.
42) I. Fujii, A. Watanabe, U. Sankawa, Y. Ebizuka, *Chem. Biol.* 2001, 8, 189.
43) T. Awakawa, K. Yokota, N. Funa, F. Doi, N. Mori, H. Watanabe, S. Horinouchi, *Chem. Biol.* 2009, 16, 613.
44) M. A. Fischbach, J. Clardy, *Nat. Chem. Biol.* 2007, 3, 353.
45) a) E. R. Vimr, L. Green, C. G. Miller, *J. Bacteria* 1983, 153, 1259; b) A. J. Barrett, M. A. Brown, *Biochem. J.* 1990, 271, 701.

What is claimed is:
1. A compound bactobolin D having a chemical structure of Structure I:

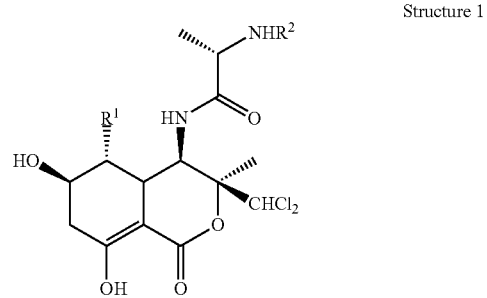

Structure 1 wherein $R^1$ is H and $R^2$ is L-Ala.

* * * * *